US012564578B2

(12) United States Patent
Xu et al.

(10) Patent No.: US 12,564,578 B2
(45) Date of Patent: Mar. 3, 2026

(54) COLLAGEN P4H1 INHIBITOR AND ITS USE

(71) Applicant: University of Kentucky Research Foundation, Lexington, KY (US)

(72) Inventors: Ren Xu, Lexington, KY (US); Shike Wang, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 1041 days.

(21) Appl. No.: 17/682,856

(22) Filed: Feb. 28, 2022

(65) Prior Publication Data

US 2022/0175742 A1 Jun. 9, 2022

Related U.S. Application Data

(63) Continuation-in-part of application No. PCT/US2020/048582, filed on Aug. 28, 2020.

(60) Provisional application No. 62/893,002, filed on Aug. 28, 2019.

(51) Int. Cl.
| | |
|---|---|
| *A61K 31/4365* | (2006.01) |
| *A61K 31/216* | (2006.01) |
| *A61K 31/337* | (2006.01) |
| *A61K 31/404* | (2006.01) |
| *G01N 33/58* | (2006.01) |

(52) U.S. Cl.
CPC ........ *A61K 31/4365* (2013.01); *A61K 31/216* (2013.01); *A61K 31/337* (2013.01); *A61K 31/404* (2013.01); *G01N 33/582* (2013.01)

(58) Field of Classification Search
CPC .............. A61K 31/4365; A61K 31/216; A61K 31/337; A61K 31/404; G01N 33/582
See application file for complete search history.

(56) References Cited

U.S. PATENT DOCUMENTS

| | | | |
|---|---|---|---|
| 9,289,415 | B2 | 3/2016 | Shi et al. |
| 9,677,117 | B2 | 6/2017 | Alves et al. |
| 10,130,590 | B2 | 11/2018 | Frank et al. |
| 2016/0280701 | A1 | 9/2016 | Raines et al. |
| 2017/0304388 | A1 | 10/2017 | Chen et al. |

FOREIGN PATENT DOCUMENTS

WO WO2019060742 3/2019

OTHER PUBLICATIONS

Promega Website https://www.promega.com/products/epigenetics/methylation-analysis/succinate-glo-jmjc-demethylase-hydroxylase-assay/?catNum=V7990&accordion0=0 Accessed Jun. 10, 2025 (Year: 2025).*

Oertli, et al., Perioperative and postoperative tranexamic acid reduces the local wound complication rate after surgery for breast cancer, British Journal of Surgery 1994, 81, pp. 856-859.
Catino, et al., Amifostine as chemoprotectant in metastatic breast cancer patients treated with doxorubicin, Oncology reports, 2003, pp. 163-167.
Pandya, et al., Gabapentin for hot flashes in 420 women with breast cancer: a randomised double-blind placebo-controlled trial, Lancet 2005; 366: 818-24.
Martin, et al., In vitro inhibitory effects of atorvastatin on cardiac fibroblasts: implications for ventricular remodeling, Clinical and Experimental Pharmacology and Physiology (2005) 32, 697-701.
Sastry, et al., Epinephrine protects cancer cells from apoptosis via activation of cAMP-dependent protein kinase and BAD phosphorylation, The Journal of Biological Chemistry vol. 282, No. 19, pp. 14094-14100, May 11, 2007.
Wang, et al, Antipsychotic drugs inhibit the function of breast cancer resistance protein, Basic & Clinical Pharmacology & Toxicology, 103, 336-341.
Li, et al., Fenofibrate induces apoptosis of triple-negative breast cancer cells via activation of NF-κB pathway, BMC Cancer 2014, 14:96, 1-13.
Romermann, et al, The antiepileptic drug lamotrigine is a substrate of mouse and human breast cancer resistance protein (ABCG2), Neuropharmacology 93 (2015) pp. 7-14.
Desai, et al, Statins and breast cancer stage and mortality in the Women's Health Initiative, Cancer Causes Control (2015) 26:529-539.
Fiorillo, et al, Repurposing atovaquone: Targeting mitochondrial complex III, Oncotarget, vol. 7, No. 23, 2016.
Provenzano, P. P.; Inman, D. R.; Eliceiri, K. W.; Knittel, J. G.; Yan, L.; Rueden, C. T.; White, J. G.; Keely, P. J., Collagen density promotes mammary tumor initiation and progression. BMC Med 2008, 6, 11.
Gorres, K. L.; Raines, R. T., Prolyl 4-hydroxylase. Crit Rev Biochem Mol Biol 2010, 45 (2), 106-24.
Zhang, H.; Fredericks, T.; Xiong, G.; Qi, Y.; Rychahou, P. G.; Li, J. D.; Pihlajaniemi, T.; Xu, W.; Xu, R., Membrane associated collagen XIII promotes cancer metastasis and enhances anoikis resistance. Breast Cancer Res 2018, 20 (1), 116.
Hanker, A. B.; Estrada, M. V.; Bianchini, G.; Moore, P. D.; Zhao, J.; Cheng, F.; Koch, J. P.; Gianni, L.; Tyson, D. R.; Sanchez, V.; Rexer, B. N.; Sanders, M. E.; Zhao, Z.; Stricker, T. P.; Arteaga, C. L., Extracellular Matrix/Integrin Signaling Promotes Resistance to Combined Inhibition of HER2 and PI3K in HER2(+) Breast Cancer. Cancer Res 2017, 77 (12), 3280-3292.
Xiong, G.; Stewart, R. L.; Chen, J.; Gao, T.; Scott, T. L.; Samayoa, L. M.; O'Connor, K.; Lane, A. N.; Xu, R., Collagen prolyl 4-hydroxylase 1 is essential for HIF-1alpha stabilization and TNBC chemoresistance. Nat Commun 2018, 9 (1), 4456.
Bickel, M.; Baringhaus, K. H.; Gerl, M.; Gunzler, V.; Kanta, J.; Schmidts, L.; Stapf, M.; Tschank, G.; Weidmann, K.; Werner, U., Selective inhibition of hepatic collagen accumulation in experimental liver fibrosis in rats by a new proly 4-hydroxylase inhibitor. Hepatology 1998, 28 (2), 404-11.

(Continued)

*Primary Examiner* — Adam C Milligan
*Assistant Examiner* — William Y Lee
(74) *Attorney, Agent, or Firm* — Stites & Harbison PLLC; Mandy Wilson Decker

(57) ABSTRACT

The present invention relates to a methods for modulating Collagen Prolyl 4-hydroxylase (C-P4H1) in a cell. The present invention further relates to methods for inhibiting a cancer cell. The instant invention also relates to methods for identifying modulators of Collagen Prolyl 4-hydroxylase (C-P4H1).

1 Claim, 20 Drawing Sheets

(56) References Cited

OTHER PUBLICATIONS

Gorres, K. L.; Raines, R. T., Direct and continuous assay for prolyl 4-hydroxylase. Anal Biochem 2009, 386 (2), 181-5.

Vasta, J. D.; Andersen, K. A.; Deck, K. M.; Nizzi, C. P.; Eisenstein, R. S.; Raines, R. T., Selective Inhibition of Collagen Prolyl 4-Hydroxylase in Human Cells. ACS Chem Biol 2016, 11 (1), 193-9.

Guo, H. F.; Cho, E. J.; Devkota, A. K.; Chen, Y.; Russell, W.; Phillips, G. N., Jr.; Yamauchi, M.; Dalby, K. N.; Kurie, J. M., A scalable lysyl hydroxylase 2 expression system and luciferase-based enzymatic activity assay. Arch Biochem Biophys 2017, 618, 45-51.

Kivirikko, K. I.; Kishida, Y.; Sakakibara, S.; Prockop, D. J., Hydroxylation of (X-Pro-Gly)n by protocollagen proline hydroxylase. Effect of chain length, helical conformation and amino acid sequence in the substrate. Biochim Biophys Acta 1972, 271 (2), 347-56.

TM488 Technical Manual, entitled "Succinate-GloTM JmjC Demethylase/Hydroxylase Assay," Mar. 2017, from Promega Corporation.

* cited by examiner

Succinate-Glo™ Hydroxylase assay   Hydroxyproline Colorimetric Assay

P4HA1

P4HA1

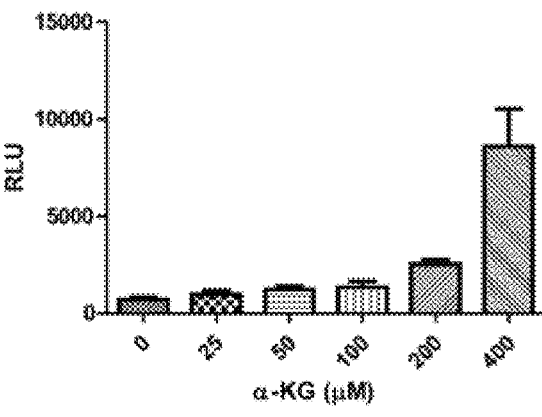
FIG. 3A
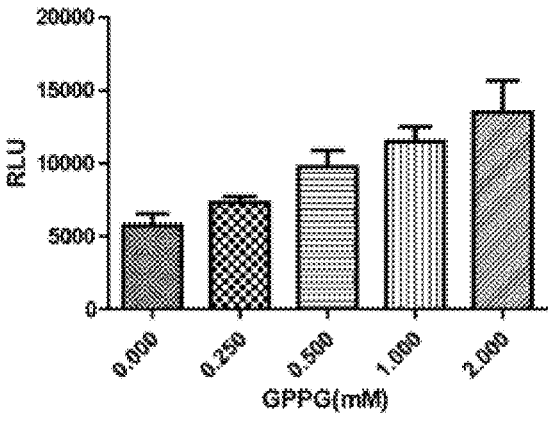
FIG. 3B
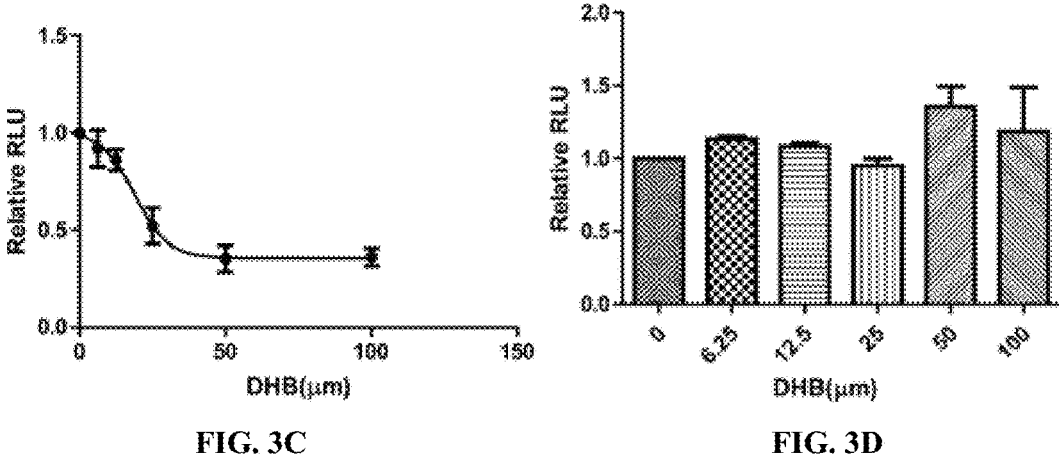
FIG. 3C　　　　　　　　　　　FIG. 3D

P4HA1

COLLAGEN P4H1 INHIBITOR AND ITS USE

RELATED APPLICATIONS

This application is a continuation-in-part of International Patent Application No. PCT/US2020/048582 filed Aug. 28, 2020, and claims priority from U.S. Provisional Application Ser. No. 62/893,002 filed on Aug. 28, 2019, the entire disclosures of which are incorporated herein by this reference.

GOVERNMENT INTEREST

This invention was made with government support under grant number CA207772 and CA215095 awarded by the National Institutes of Health. The government has certain rights in the invention.

SEQUENCE LISTING

This application contains a sequence listing submitted in accordance with 37 C.F.R. 1.821, named 13177N 2310US XU sequence listing.txt, created on Aug. 18, 2020, having a size of 473 bytes, which is incorporated herein by this reference.

TECHNICAL FIELD

The present invention relates to methods of inhibiting and activating Collagen P4H1. The invention also relates to methods for inhibiting breast cancer cells and treating breast cancer by inhibiting Collagen P4H1.

BACKGROUND

Collagen is the most abundant extracellular matrix (ECM) protein in human body[1]. Increased collagen expression and deposition are associated with fibrosis and tumor progression, and reducing collagen production is sufficient to inhibit the progression of these diseases[2-4]. Collagen is synthesized and forms the triple helix structure in the ER[5]. The basic unit of the triple-helical structure is Gly-pro-X, and the proline is often hydroxylated. Prolyl hydroxylation is required for the sharp twisting of collagen helix and secretion of collagen protein[6]. Therefore, the proline hydroxylation pathway is considered a promising target to halt collagen expression and deposition.

Collagen hydroxylation is catalyzed by collagen prolyl 4-hydroxylase (C-P4H)[7], a $Fe^{2+}$ and 2-oxoglutarate-dependent enzyme[7]. C-P4H contains two α subunits (P4HA) and two β subunits (P4HB), and each a subunit contains the peptide substrate binding domain and the catalytic domain[8]. Three P4HA isoforms have been characterized in mammalian cells with different tissue distribution. It has been shown that P4HA1 contributes more than 50% of prolyl 4-hydroxylase activity in most cell types and considered the major isoform[9].

Increased collagen expression or deposition is associated with cancer development, such as gastric cancer[10], breast cancer[11], bladder cancer[12], and colorectal cancer[13]. Binding of collagen to its receptors such as discoidin domain receptors (DDRs)[14] and integrin[15, 16] activates downstream signal pathways, and subsequently enhances cancer cell migration and invasion[17, 18]. It has been shown that P4HA1 expression is induced during cancer development and progression. Silence of P4HA1 is sufficient to inhibit cancer metastasis and sensitize cancer cells to chemotherapeutic agents[19].

Increased P4HA1 expression has also been detected in fibrosis, and inhibition of P4HA1 reduces hepatic collagen accumulation and suppresses the fibrosis progression[20]. Overexpression of P4HA1 increases atherosclerotic plaque in apolipoprotein E-deficient mice, suggesting a potential role of P4HA1 in coronary thrombosis[21]. These results suggest that P4HA1 is a potential therapeutic target for cancer and fibrosis.

A HPLC-based assay has been developed to measure C-P4H1 activity based on P4H-catalyzed turnover of a flp-containing peptide[22]. This assay has been utilized to examine small molecule activities in the small scale, resulting in the identification of several chemicals as C-P4H1 inhibitor, including ethyl-3,4-dihydroxybenzoic acid (DHB) and 2,2'-bipyridine (bipy)[23, 24]. Although their inhibitory activities on collagen secretion has been confirmed in tissue culture, none of them has been approved for clinical use. There is an urgent need to identify potent C-P4H1 inhibitors that can be used in clinic for the treatment of collagen-dependent diseases.

A novel method to measure C-P4H1 activity by quantifying the product of prolyl hydroxylation, succinate is described herein. A high throughput screening assay was developed based on this method and identified Silodosin and Ticlopidine as novel C-P4H1 inhibitors from the FDA-approved drug library. Further examining their biological activity in vivo may identify Silodosin and Ticlopidine as potential drugs targeting C-P4H1-dependent diseases.

SUMMARY

In accordance with the purpose(s) of the invention, as embodied and broadly described herein, the invention, in one aspect, relates to methods of inhibiting a cancer cell, comprising: administering to the cancer cell an effective amount of a compound selected from the group consisting of: tripelennamine, fluvastatin, gabapentin, L-adrenaline, methacycline, fenfibrate, beclomethasone dipropionate, roflumilast, promethazine, ticlopidine, amifostine, dinaciclib, pramipexole, bromfenac, flavopiridol, flutamide, sitagiptin, racecadotril, vinblastine, salbutamol, pemetrexed, atovaquone, olanzapine, procainamide, bicalutamide, clindamycin, nafcillin, cysteamine, poziotinib, lomefloxacin, axitinib, valdecoxib, scopolamine, R-atenolol, sildosin, lamotrigine, levobetaxolol, bosentan, ledipasvir, pralatrexate, gabapentin, epinephrine, erlotinib, mesnex, rofecoxib, mezlocillin, serotonin, tranexamic acid, or combinations thereof, to the cell. In some embodiments, the cancer cell is a breast cancer cell or lung cancer cell. In other embodiments, the cancer cell is in a subject. In further embodiments of the present invention the compound used to inhibit a cancer cell is silodosin, fenofibrate, ticlopidine, or combinations thereof. In certain embodiments, the effective amount of silodosin or ticlopidine is from about 10 µM to about 200 µM. In further embodiments, docetaxel is also administered. In some embodiments, the effective amount of fenobibrate is about 40 mg/kg.

Another embodiment of the instant invention is a method of inhibiting Collagen Prolyl 4-hydroxylase (C-P4H1) in a cell, comprising: administering to the cell an effective amount of (a) a compound selected from the group consisting of: tripelennamine, fluvastatin, gabapentin, L-adrenaline, methacycline, fenfibrate, beclomethasone dipropionate, roflumilast, promethazine, ticlopidine, amifostine, dinaciclib, pramipexole, bromfenac, flavopiridol, flutamide, sitagiptin, racecadotril, vinblastine, salbutamol, pemetrexed, atovaquone, olanzapine, procainamide, bicalutamide, clindamycin, nafcillin, cysteamine, poziotinib, lomefloxacin, axitinib, valdecoxib, scopolamine, R-atenolol, sildosin, lamotrigine, levobetaxolol, bosentan, ledipasvir, pralatrexate, gabapentin, epinephrine, erlotinib, mesnex, rofecoxib, mezlocillin, serotonin, tranexamic acid, or combinations thereof or (b) a compound selected from the group consisting of pimavanserin, modafinil, quinapril, rosiglitazone, sulconazole, GSK2126458, cinepazide, methylthiouracil, EPZ-6438, ethosuximide, roxithromycin, atorvastatin, penfluridol, lonafarnib, foscarnet, allylthiourea, halothane, milrinone, maprotiline, famotidine, L-thyroxine, tideglusib, moruisteine, guaifenesin, hydroquinone, nitrendipine, mecarbinate, pramoxine, buflomedil, evacetrapib, oxybutynin, flavoxate, or combinations thereof.

Another embodiment of the present invention is a method of inhibiting C-P4H1 in a cell, comprising: administering to the cell an effective amount of a compound selected from the group consisting of: tripelennamine, fluvastatin, gabapentin, L-adrenaline, methacycline, fenfibrate, beclomethasone dipropionate, roflumilast, promethazine, ticlopidine, amifostine, dinaciclib, pramipexole, bromfenac, flavopiridol, flutamide, sitagiptin, racecadotril, vinblastine, salbutamol, pemetrexed, atovaquone, olanzapine, procainamide, bicalutamide, clindamycin, nafcillin, cysteamine, poziotinib, lomefloxacin, axitinib, valdecoxib, scopolamine, R-atenolol, sildosin, lamotrigine, levobetaxolol, bosentan, ledipasvir, pralatrexate, gabapentin, epinephrine, erlotinib, mesnex, rofecoxib, mezlocillin, serotonin, tranexamic acid, or combinations thereof.

One embodiment of the present invention is a method of activating C-P4H1 in a cell, comprising: administering an effective amount of a compound selected from the group consisting of: pimavanserin, modafinil, quinapril, rosiglitazone, sulconazole, GSK2126458, cinepazide, methylthiouracil, EPZ-6438, ethosuximide, roxithromycin, atorvastatin, penfluridol, lonafarnib, foscarnet, allylthiourea, halothane, milrinone, maprotiline, famotidine, L-thyroxine, tideglusib, moruisteine, guaifenesin, hydroquinone, nitrendipine, mecarbinate, pramoxine, buflomedil, evacetrapib, oxybutynin, flavoxate, or combinations thereof.

Another embodiment of the present invention includes a method of screening for modulators of C-P4H1, comprising:
(a) expressing a P4H1 complex in a eukaryotic cell;
(b) purifying the P4H1 complex;
(c) adding the purified P4H1 complex to a well of a high throughput assay plate;
(d) adding peptide substrate (GlyProProGly(SEQ ID NO:1)OEt), 500 μM), FeSO4 (50 μM), catalase (0.1 mg/mL), ascorbate (2 mM), and α-ketoglutarate (100 μM) to the well of the high throughput assay plate for 1 hour;
(e) adding a test molecule or control to the well of the high throughput assay plate;
(f) adding enzymes that convert succinate into ATP to the well of the high throughput assay plate;
(g) adding luminescent enzymes that convert ATP into light energy to the well of the high throughput assay plate;
(h) measuring luminescence of the well of the high throughput assay plate; and
(i) identifying a molecule as a modulator of P4H1 when the molecule increases luminescence of the well relative to negative control or decreases luminescence of the well relative to positive control.
In some embodiments, the luminescent enzyme is luciferase.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein:

FIG. 1A. Expression of C-P4H1 was analyzed by western blot with anti-P4H1α and anti-flag antibody. Cell lysates were collected from control and 293FT cells transfected with P4HA1 and P4HB constructs.

FIG. 1B. Ponceau staining showed the expression and purification of C-P4H1 from 293 FT cells and CHO cells. The letters indicate: L (Total cell lysates with HGLB), Un (unbinding samples after cell lysates incubated with M2 gel), W (The last time washed sample in NET2), E1 (The first time elution sample in 0.25 μg/μL 3*Flag), E2 (The second time elution sample in 0.25 μg/μL 3*Flag), Gel (The remaining sample on M2 gel after elution).

FIG. 1C. Western blot analysis of C-P4H1 expression and purification with anti-P4Ha.

FIG. 1D. Purified P4H1 samples was analyzed by 8% Native PAGE gel with Coomassie Blue staining; BSA was included as a control.

FIG. 1E. Anti-flag and anti-P4HA1 antibodies were used to verify the purification protein.

FIG. 2A. Scheme showing collagen hydroxyproline reaction.

FIG. 2B. Scheme showing how the Succinate-Glo™ Hydroxylase assay (Left) which was developed to detect succinate, and how Hydroxyproline Colorimetric Assay (Right) was used to detect the HO-GPPG.

FIG. 2C. C-P4H1 activity was evaluated with the Hydroxyproline Colorimetric Assay at different concentrations. n=3. * means P value<0.05. One-way anova analysis.

FIG. 2D. C-P4H1 activity was measured with the Succinate-Glo™ Hydroxylase assay at different concentrations. n=3. ** means P value<0.01. One-way anova analysis.

FIG. 2E. MT-P4HA1 activity was evaluated with the Succinate-Glo™ Hydroxylase assay at different concentrations. n=3. ns, no statistical significance. The data displayed as means+/−standard deviation (SD).

FIG. 2F. Wild-type (WT) C-P4HA1 and Mutant (483)-type C-P4HA1 reaction with different concentration.

FIG. 2G. 0.1 μM WT C-P4HA1 reacts with different concentration α-KG.

FIG. 2H. 0.1 μM WT C-P4HA1 reacts with different concentration peptide (GPPG).

FIGS. 3A-3E show evaluation of the Succinate-Glo™ Hydroxylase assay for analyzing C-P4H1 activity.

FIG. 3A. Bar graph showing the C-P4H1 (200 nM) activity at different concentrations of 2-KG. n=3.

FIG. 3B. Bar graph showing the C-P4H1 (200 nM) activity at different concentrations of substrate peptide Gly-ProProGly(SEQ ID NO: 1)OEt (GPPGOEt). n=3.

FIG. 3C. Curve measurement of the inhibitory activity of DHB in C-P4H1 (200 nM) reaction. All the ATP signals produced by the plate reader were normalized with control. n=3.

FIG. 3D. DHB did not inhibit the Succinate-Glo™ Hydroxylase assay in the absence of WT-P4H1. All the ATP signals produced by the plate reader were normalized with control. n=3.

FIG. 3E. 0.1 μM WT and mutant 483 C-P4HA1 react with different concentration with DHB.

FIG. 4A. The frequency for relative activity of P4H1 at the presence of each molecule. Over 1400 FDA approved drugs (test molecules) were screening in the 384 well plate or 96-well plate at 50 μM. 50 μM DHB was used as a positive control in each plate. All the ATP signals generated from the Succinate-Glo™ Hydroxylase assay were normalized with vehicle control (negative control). The * indicated that the relative activity of C-P4H1 in the presence of DHB.

FIG. 4B. Plot showing chemical number as a function of relative activity.

FIG. 4C. In vitro activity of C-P4HA1 treated with 50 μM compounds.

FIG. 4D. Silodocin inhibitory activity was analyzed at different concentrations. All the ATP signals produced by the plate reader were normalized to vehicle control, control value is 1; n=3.

FIG. 4E. Silodocin did not inhibit the Succinate-Glo™ Hydroxylase assay in the absence of WT-P4H1; n=3.

FIG. 4F. Ticlopidine inhibitory activity was analyzed at different concentrations; 200 nM C-P4H1 in the reaction. The C-P4H1 activities in ticlopidine treated samples were normalized with vehicle control, control value is 1; n=3.

FIG. 5A. Western blot analyzed levels of type I collagen in conditional medium of HS578 cells, The cells were treated with Silodosin at 10 μM and 20 μM.

FIG. 5B. Western blot analyzed levels of type I collagen in conditional medium of HS578 cells, The cells were treated with Ticlopidine at 10 μM and 20 μM.

FIG. 5C. Invasiveness of MDA-MB-231 cells was examined in 3D culture assay in the presence or absence of Silodosin and Ticlopidine. The cells were with Silodosin or Ticlopidine at 10 μM and 20 and images were taken after 48 hours. Scale bar, 100 μm.

FIG. 5D. Dot blot graph quantified invasive branching structures in panel C. One-way ANOVA analysis; n≥20; ***means P≤0.001.

FIG. 5E. Phase images of control and Hs-578 cells treated with Silodosin and Ticlopidine at 10 μM and 20 μM in 3D culture assay. Images were taken at 24 hours after treatment. Scale bar, 100 μm.

FIG. 5F. Dot blot graph quantified invasive branching structures in panel E. One-way ANOVA analysis; n≥20. ***means P≤0.001.

Figure 1A:
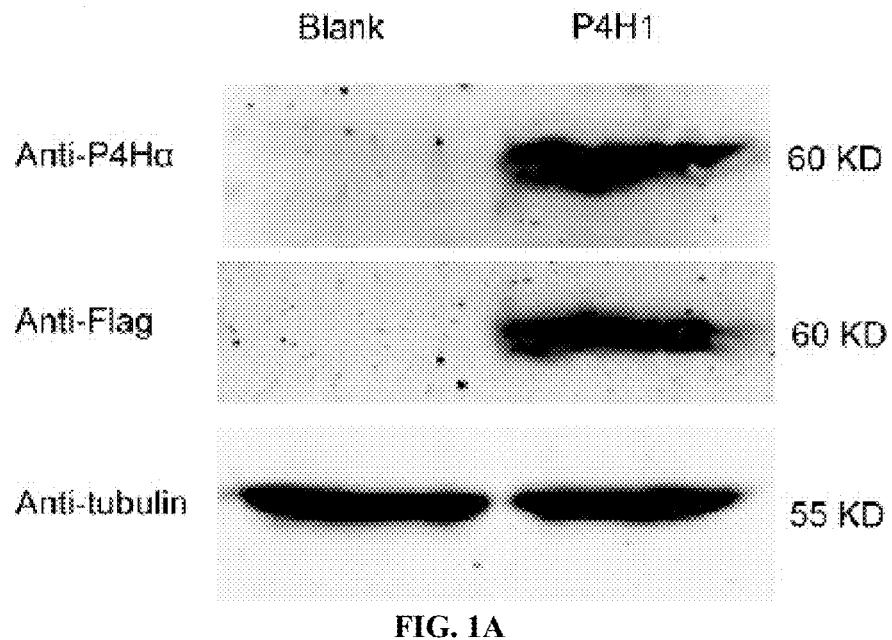
FIG. 1A-1E show C-P4H1 is expressed and purified from HEK-293FT cells.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

Definitions

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, and in some embodiments ±0.01% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "subject" refers to a target of administration. The subject of the herein disclosed methods can be a mammal. Thus, the subject of the herein disclosed methods can include a mouse or human. The term does not denote a particular age or sex.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "modulator(s)" of a protein such as C-P4H1 refers to molecules can either increase or decrease the activity of C-P4H1. A modulator can function in vitro or in vivo. In some aspects, the increase or decrease in activity can be determined relative to a control condition. In some embodiments, the increase or decrease in activity can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% relative to a control. In some embodiments of the instant invention, DHB is used as a positive control in screening assays, in other embodiments, a vehicle control is used as a negative control in screening assays. Modulating a proteins such as C-P4H1 can refer to activity of said protein increasing or decreasing in the presence of a modulator.

The term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level if or any particular patient will depend upon a variety of factors including the disorder being treated and the severity of the disorder; the specific composition employed; the age, bodyweight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. One example in the instant invention is an effective amount of a P4H1 inhibitor As used herein, the term "inhibiting a cancer cell" refers to any action which decreases the success of cancer cell proliferation. Actions which decrease the success of cancer cell proliferation include but are not limited to: inhibiting, reversing, or preventing the growth, division, metastasis, or invasion of a cancer cell. In some instances, inhibition of a cancer cell can be accomplished by a molecule that inhibits P4H1.

Examples

The presently-disclosed subject matter is further illustrated by the following specific but non-limiting examples. The following examples may include compilations of data that are representative of data gathered at various times during the course of development and experimentation related to the present invention.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1—Materials and Methods

Cell Culture and 3D Culture Assay

MDA-MB-231 cells (ATCC) were cultured in DMEM/F12 (Sigma) with 10% fetal bovine serum (Invitrogen). HS-578 cells (ATCC) were cultured in DMEM (Sigma) with 10% fetal bovine serum.

3D laminin-rich extracellular matrix (3D lrECM) on-top cultures were prepared by trypsinization of cells from tissue culture plastic[25]. Growth Factor Reduced BD Matrigel™ was plated on the bottom of the cell culture dish. MDA-MB-231 and HS-578 cells were seeded on the top of the matrigel layer, and additional medium containing 10% Matrigel was added on the top.

Cell Viability Assay

To analyze cell viability in response to drug treatment, MDA-MB-231 and HS-578 cells were seeded into 96-well plate with the density of 3000 cells per well. Following the cell adhesion, chemicals were added and treating 48 hours. The cell viability was measured by the cell counting kit-8 (sigma).

CP4H1 Expression and Purification pcDNA 3.1-CP4Hα-flag and pcDNA 3.1-CP4Hβ-flag plasmids were constructed and transfected into 293FT cells with the Fugene reagent (Promega). Following 48 hours' transfection, cells were washed by PBS and lysed with HGLB (10 mM Tris-HCl pH 7.5, 10 mM NaCl, 2 mM EDTA, 0.5% Triton X-100) containing 1*cocktail proteinase inhibitors (Calbiochem). Lysates were incubated with M2 gel (Sigma) at cold room for at least 4 hours, washed with NET2 buffer, and then eluted with 250 µg/mL 3*flag peptide (GP10149). The solution containing CP4H1 was concentrated with centrifugal filters (Millipore) and replaced with protein storing buffer (150 mM NaCl, 50 mM HEPES pH 7.4). The purified CP4H1 was subjected to native gel or SDS-PAGE gel.

Western Blot

Chemical treated Hs578 cells were lysed in 2% sodium dodecyl sulfate (SDS) in phosphate-buffered saline (PBS) buffer containing phosphatase and protease inhibitor cocktails (EMD Millipore, 539131). Protein concentration was measured using Pierce™ BCA Protein Assay Kit (Thermo Fisher Scientific, 23227). Equal amounts of protein lysates or cell conditional medium (normalized to cell numbers) were subjected to SDS gel electrophoresis, immunoblotted with primary antibodies (Anti-Collagen I antibody, ab34710; Anti-tubulin, Cell Signaling 2148)) and DyLight 680/800-conjugated secondary antibodies (DyLight 680-conjugated goat anti-rabbit IgG secondary antibody Thermo Fisher Scientific, 35569; DyLight 800-conjugated goat anti-mouse IgG secondary antibody Thermo Fisher Scientific, SA5-35521).

Measuring Human CP4H1 Activity with Hydroxyproline Colorimetric Assay and Succinate-Glo™ Hydroxylase Assay Human CP4H1 Activity Assay Human CP4H1 activity Assays were carried out at room temperature in 10 mM HEPES buffer containing 10 mM NaCl, pH 7.4. Mix with human CP4H1 (200 nM), peptide substrate (GlyProProGly(SEQ ID NO:1)OEt), 500 µM), $FeSO_4$ (50 µM), catalase (0.1 mg/mL), ascorbate (2 mM), and α-ketoglutarate (100 µM). $FeSO_4$ was prepared freshly in 10 mM HCl prior to each time use. Following 1 hour reaction, the reaction solution was subjected to Hydroxyproline Colorimetric Assay and Succinate-Glo™ Hydroxylase assay respectively.

Hydroxyproline Colorimetric Assay

Hydroxyproline Colorimetric Assay was described as below. Add 100 µl of the Chloramine T reagent (0.282 g chloramine-T, 1 mL n-propanol, 1 mL demineralized water and 8 mL stock buffer, stock buffer consisting of 0.24 M citric acid, 0.88 M sodium acetate trihydrate, 0.88 M anhydrous sodium acetate, 0.21M acetic acid and 0.85 M sodium hydroxide, pH 6.1) to each hydroxyproline sample and incubate at room temperature for 5 min. Add 100 µl of the DMAB reagent (2 g dimethylaminobenzaldehyde dissolved in 1.25 mL n-propanol and 2.75 mL perchloric acid) to each well and incubate for 90 min at 60° C. Measure absorbance at 560 nm in a microplate reader (BioTek).

Succinate-Glo™ Hydroxylase Assay

Succinate-Glo™ Hydroxylase assay was ran following the protocol of Succinate-Glo™ JmjC Demethylase/Hydroxylase Assay (Promega, V7991). Briefly, following the human CP4H1 assay, 10 µL Succinate Detection Reagent I was added, including the enzymes 3-oxoacid CoA-transferase (SCOT) and succinyl CoA ligase (SCS), and acetoacetyl-CoA. See, TM488 Technical Manual and U.S. Pat. No. 9,677,117 for "Bioluminescent Succinate Detection Assay," issued Jun. 13, 2017, assigned to Promega Corporation. Mix assay plate with a plate shaker for 30 seconds, and incubate at room temperature for 60 minutes. Add 20 µl of Succinate Detection Reagent II, including the enzyme luciferase, to each well of the assay plate to generate light from the ATP. See, Id. Mix assay plate with a plate shaker for 30 seconds, and incubate at room temperature for 10 minutes. Measure the luminescence with a plate-reading luminometer (BioTek).

High-Throughput Screening

All the chemicals (50 μM) were incubated with human C-P4H1 (200 nM) at least 30 min on ice. Then mix with peptide substrate (GlyProProGly(SEQ ID NO:1)OEt), 500 μM), FeSO$_4$ (50 μM), catalase (0.1 mg/mL), ascorbate (2 mM), and α-ketoglutarate (100 μM) to react 1 hour at room temperature. The reaction volume was usually 10 μL. After the reaction, Succinate-Glo™ Hydroxylase assay was conducted in the corresponding 96-well or 384-well plate. 50 μM DHB was set as a positive control in each plate.

Statistical Analysis

All the 3D culture assay images were acquired by Nikon microscope and were quantified with the Nikon analysis software. Results are reported as mean±S.E.M; the significance of difference was assessed by independent Student's t-test. P<0.05 represents statistical significance and P<0.01 represents sufficiently statistical significance. All reported P values were 2-tailed.

Example 2—Protein Expression and Purification

C-P4H1 contains two al subunits and two subunits. The subunit is the protein disulfide isomerase (PDI)[26], which is required for catalytic activity of the a subunit[27]. Therefore, it is necessary to purify the C-P4H1 tetramer for measuring its activity. In previous studies, C-P4Hs were often expressed and purified from E. coli[28]. Given the important function of post modification for protein activity, mammalian cell lines for C-P4H1 expression were used. HEK-293 FT and CHO have been widely used to expression exogenous proteins with high transfection efficiency[29]. P4HA1 and P4HB expression constructs with flag tag were transfected into HEK-293FT cells. The cells were harvested 48 hours after transfection, and P4HA1 expression was examined by western blotting with antibodies against P4HA1 and Flag (FIG. 1A).

Figure 1B:
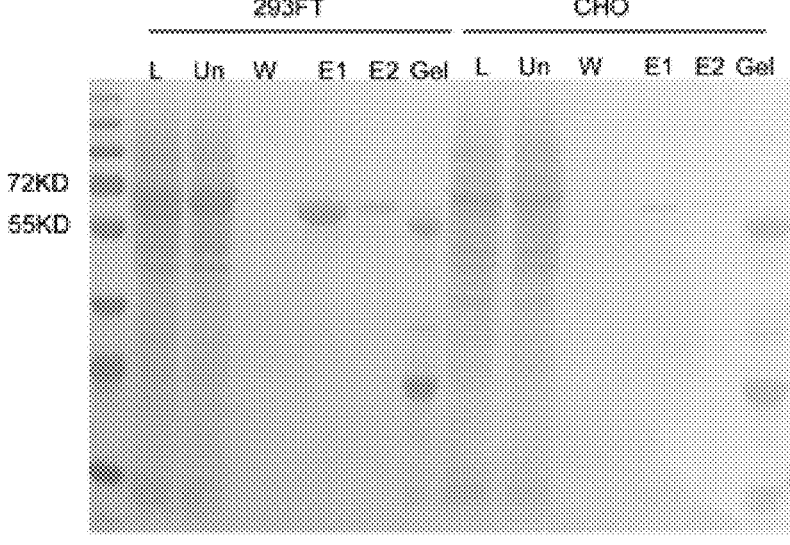
Figure 1C:
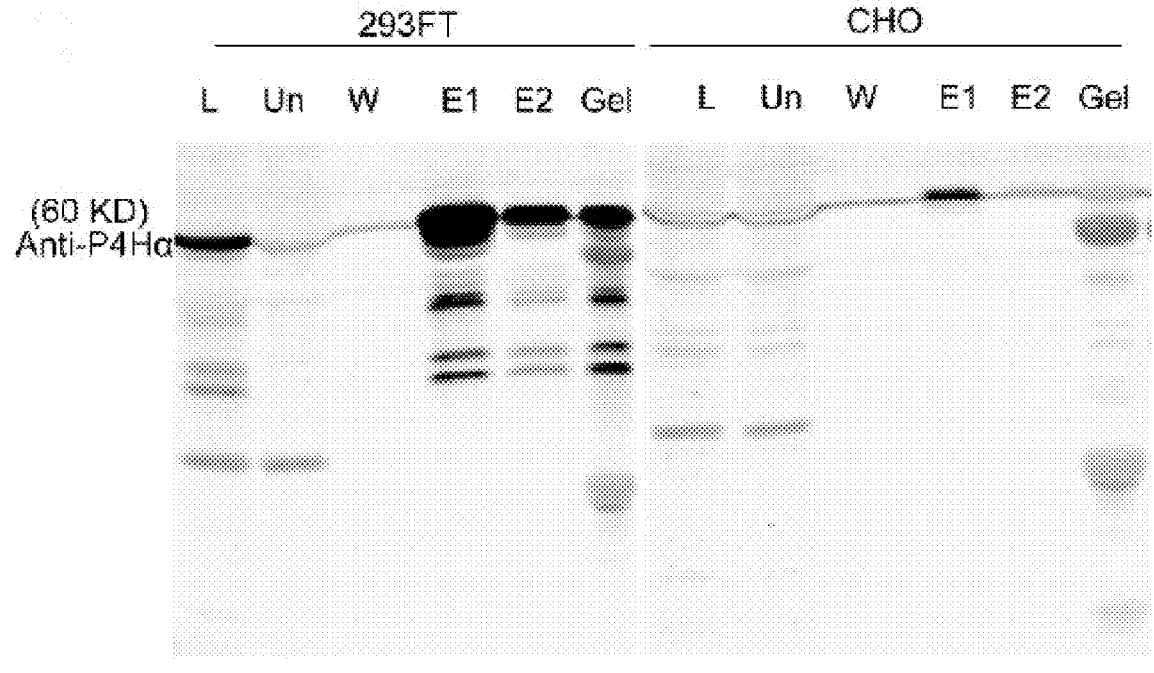

Next, C-P4H1 expression in HEK-293FT cells and CHO cells was compared. P4HA1 and P4HB expression constructs were transfected into these two cell lines, and the recombinant C-P4H1 was purified with anti-Flag M2 beads. P4H al was expressed and purified at much higher levels in HEK-293FT cells than in CHO cells (FIGS. 1B and 1C). Therefore, HEK-293FT cells were utilized to generate C-P4H1 for the following experiments.

Figure 1D:
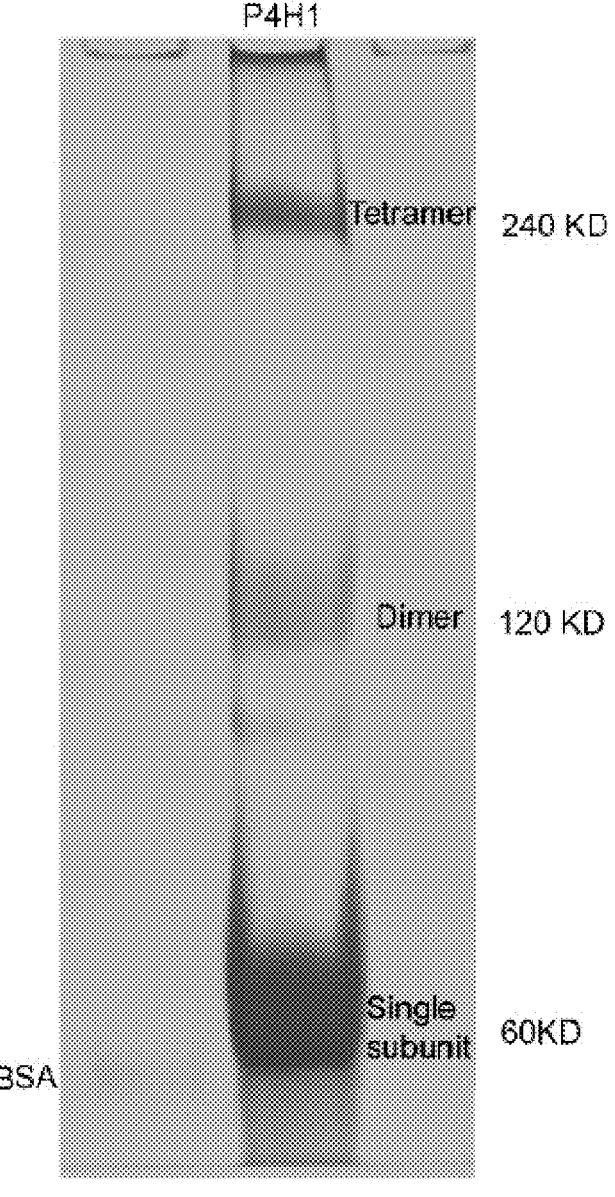
Figure 1E:
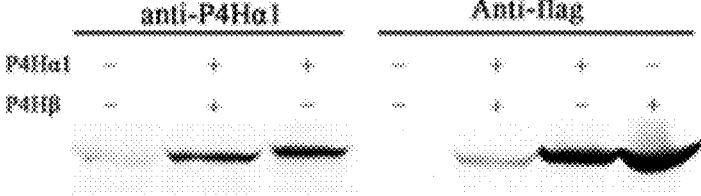

To determine whether the C-P4H1 tetramer was purified with anti-Flag M2 beads, native gel electrophoresis was performed to analyze the purified protein. Coomassie blue staining results showed that the purified protein presented at three major bands, and tetramer, dimer and single subunit were all detected (FIG. 1D). Anti-flag and anti-P4HA1 antibodies were used to verify the purification protein (FIG. 1E). The Anti-flag band was at the same location with anti-P4HA1 band, indicating that P4HA1 is purified and exists in tetramer.

Example 3—Screening Method Confirmation

Figure 2A:
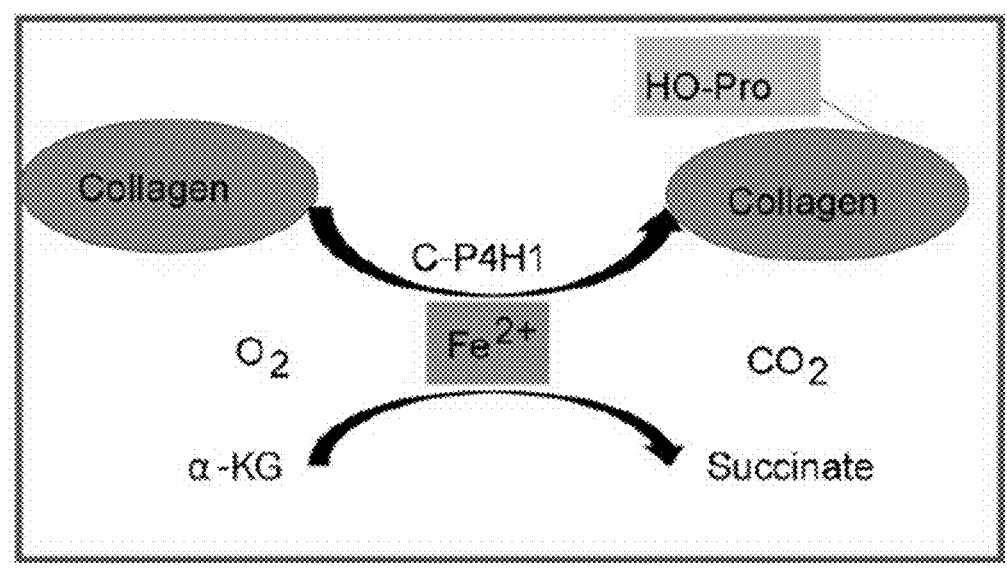
FIGS. 2A-2H relate to a hydroxyproline colorimetric assay and a succinate-Glo™ hydroxylase assay developed to analyze C-P4H1 activity.
Figure 2B:
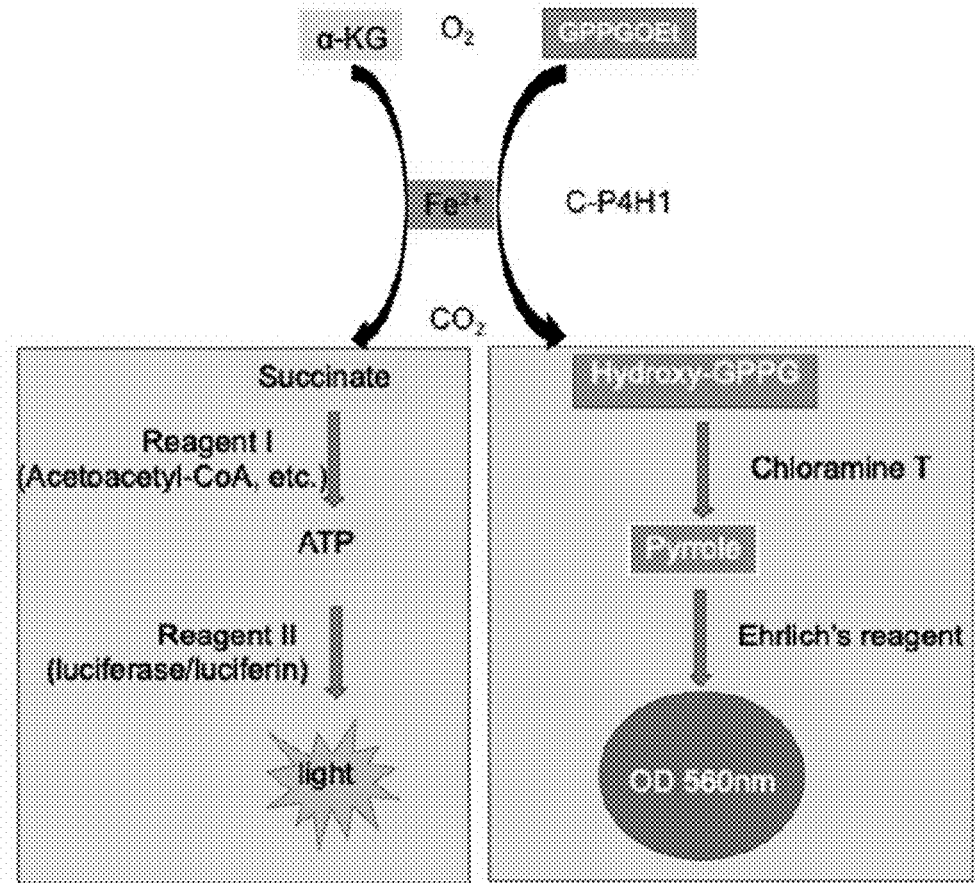
Figure 2C:
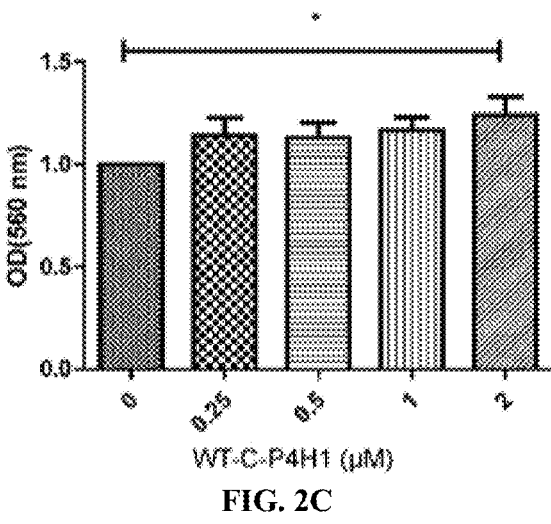
Figure 2D:
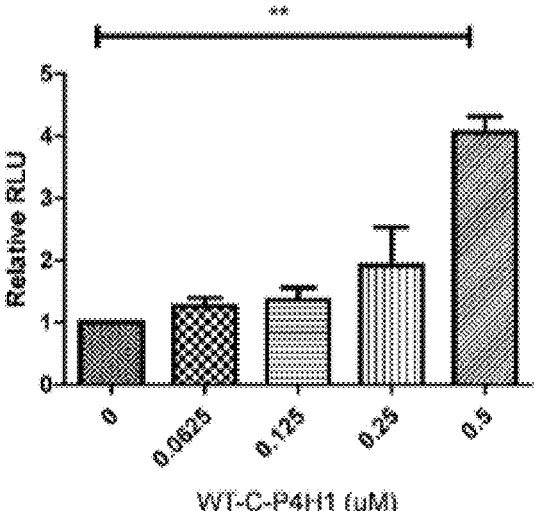

The colorimetric assay has been used to evaluate hydroxyproline and quantified collagen levels in ECM[30-32], in which hydroxyproline reacts with p-dimethylaminobenzaldehyde (DMAB, Ehrlich's reagent) to produce the chromophore (FIG. 2B). However, this assay has not been used to characterize C-P4Hs inhibitors. Bioluminescence-based Succinate-Glo™ Hydroxylase assay (FIG. 2B) has been used to measure protein hydroxylase activity with the high content potential[33]. The two assays were compared with different concentration of C-P4H1. The OD$_{560}$ value in the hydroxyproline reaction was moderately increased at 0.25 uM C-P4H1 compared to negative control, and further increasing the concentration of C-P4H1 had little effect on the OD value (FIG. 2C). Luminescence values in the Succinate-Glo™ assay were induced by C-P4H1 in a dose dependent manner, and two fold induction was detected at 0.25 uM of C-P4H1(FIG. 2D). These results indicate that the bioluminescence-based Succinate-Glo™ assay is more sensitive for evaluating C-P4H1 activity.

Figure 2E:
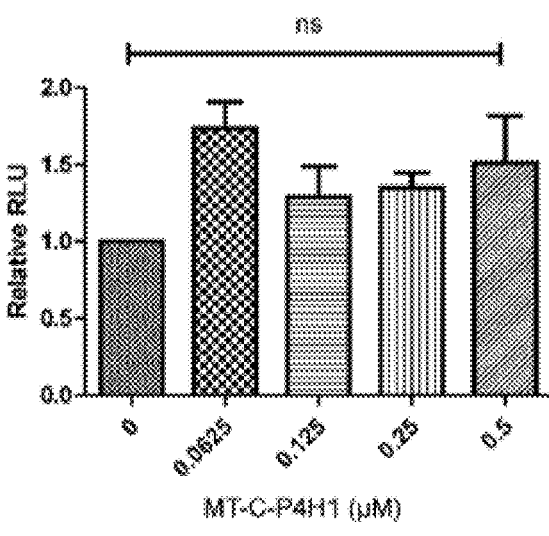
Figures 2F, 2G, 2H:
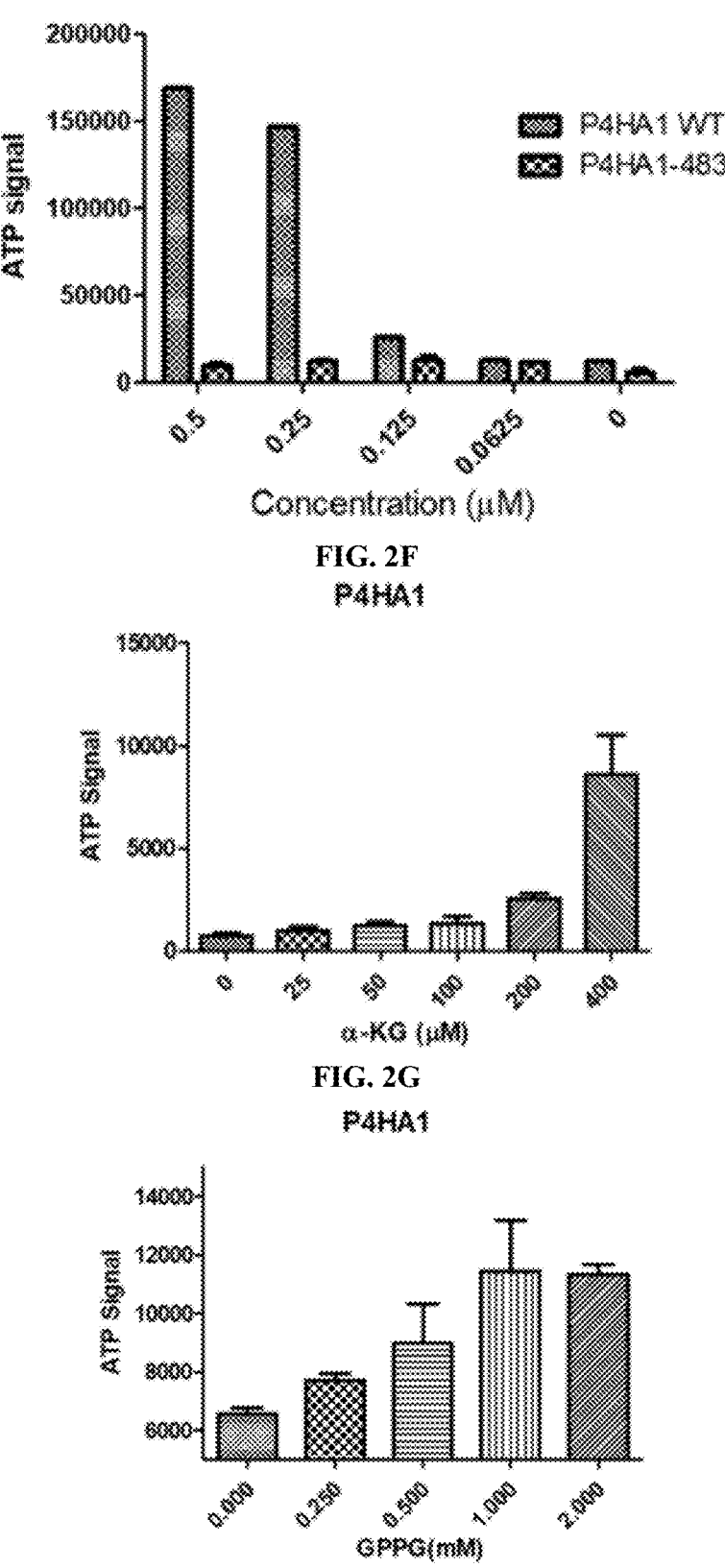

It has been shown that mutation of P4HA1 H483 abolished the prolyl hydroxylase activity without any impact on tetramer formation[34]. The mutant P4HA1 H483 S were cloned into pcDNA 3.1 vector. The mutant protein (MT-C-P4H1) was expressed in HEK-293FT cells and purified using the same protocol with the wild type C-P4H1 (WT-C-P4H1). Mutant C-P4H1 failed to increase the luminescence values in the Succinate-Glo™ assay (FIG. 2E). These results indicate that Succinate-Glo™ assay specifically detects prolyl hydroxylase activity of C-P4H1. Succinate production was induced with increased concentration of wild type C-P4H1, while the hydroxylation-deficient mutant did not induce succinate production (FIG. 2F). The assay was also tested using different concentration of GPPG and αKG. Similarly, the production of succinate depends on the concentration of GPPG and αKG (FIG. 2G and FIG. 2I). The assay that was developed can be used to measure C-P4H1 activity and identify C-P4H1 inhibitors.

Figure 3E:
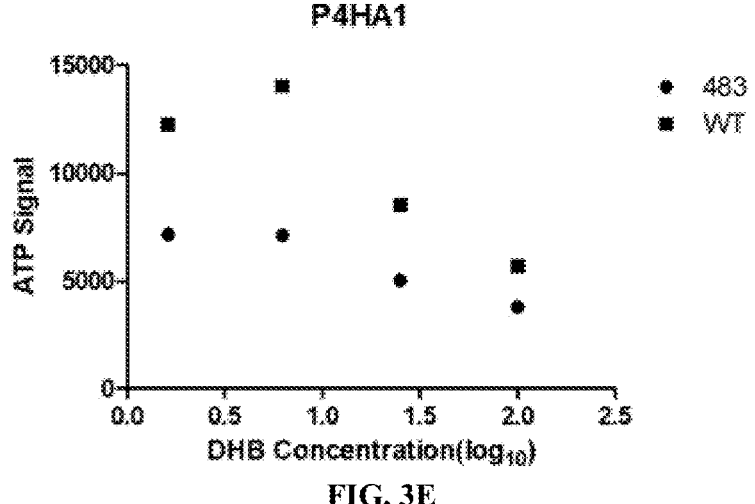

To further evaluate reliability of the Succinate-Glo™ assay, varied concentration of peptide substrate GPPG (FIG. 3A) and hydroxyl donor α-KG (FIG. 3B) were tested in the hydroxylation reaction, respectively. Increased concentration of GPPG and α-KG induced luminescence assay in a dose dependent manner. DHB has been identified as a C-P4Hs' inhibitor[35]. To determine whether this assay can evaluate c-P4H1 inhibitor's activity, C-P4H1 was incubated with different concentration of DHB for 30 min at 4° C., and then the hydroxylation reaction and the bioluminescence-based assay were performed. Treatment with DHB significantly reduced luminescence values (FIG. 3C). The IC50 was detected at around 20 μM, which is much lower than the IC50 value of 0.1 mM reported in the previous research with the collagen hydroxylation assay in the chicken tendon cells (doi: 10.1042/bj2610127); this is probably due to the sensitivity difference between two methods. In the absence of C-P4H1, DHB had little effect on the Succinate-Glo™ assay, indicating the inhibitory effect is specific on the prolyl hydroxylation reaction (FIG. 3D). These results demonstrate that the bioluminescence-based Succinate-Glo™ Hydroxylase assay can be used to screen C-P4H1 inhibitors. The results showed that DHB could significantly inhibit the enzyme activity of the wild type C-P4H1 but not the mutant protein in a dose dependent manner (FIG. 3E) in this assay, and the IC50 is about 40 μM.

Example 4—Inhibitory Screening and Verification

Figure 4A:
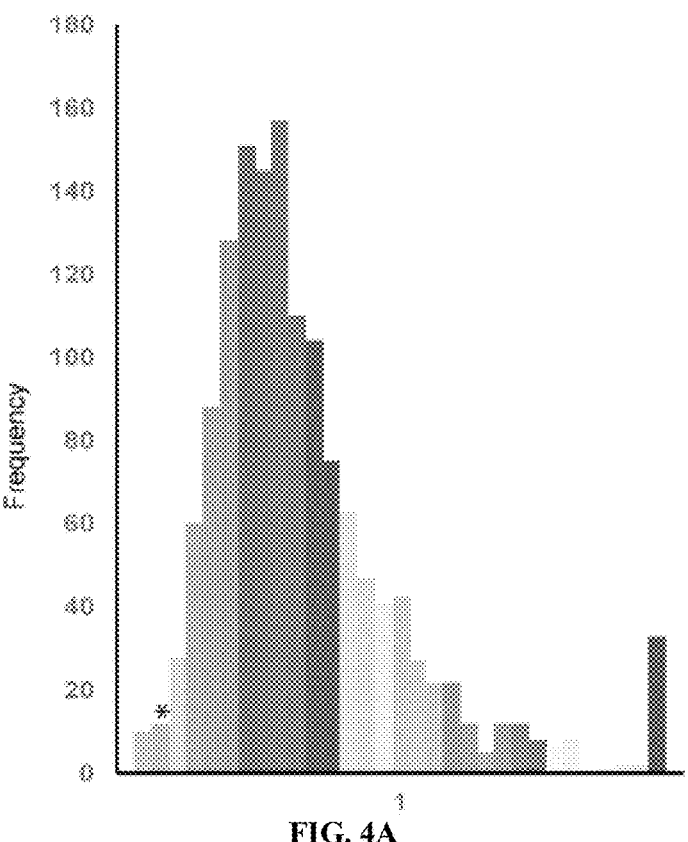
FIGS. 4A-4F show C-P4H1 inhibitors are identified with the high-throughput screening assay from the FDA-approved drug library.

Repurposing FDA-approved drugs is a popular strategy to facilitate clinical studies of new therapeutic targets[37]. To identify new C-P4H1 inhibitors that can be tested in clinic, a moderate scale screening with the bioluminescence-based assay using more than 1400 FDA approved chemicals was performed. were identified over 40 chemicals (FIG. 4A) with greater or similar inhibitory ability compared to DHB. The inhibitory activities of two drugs, Silodosin and Ticlo-

13

Figure 4B:
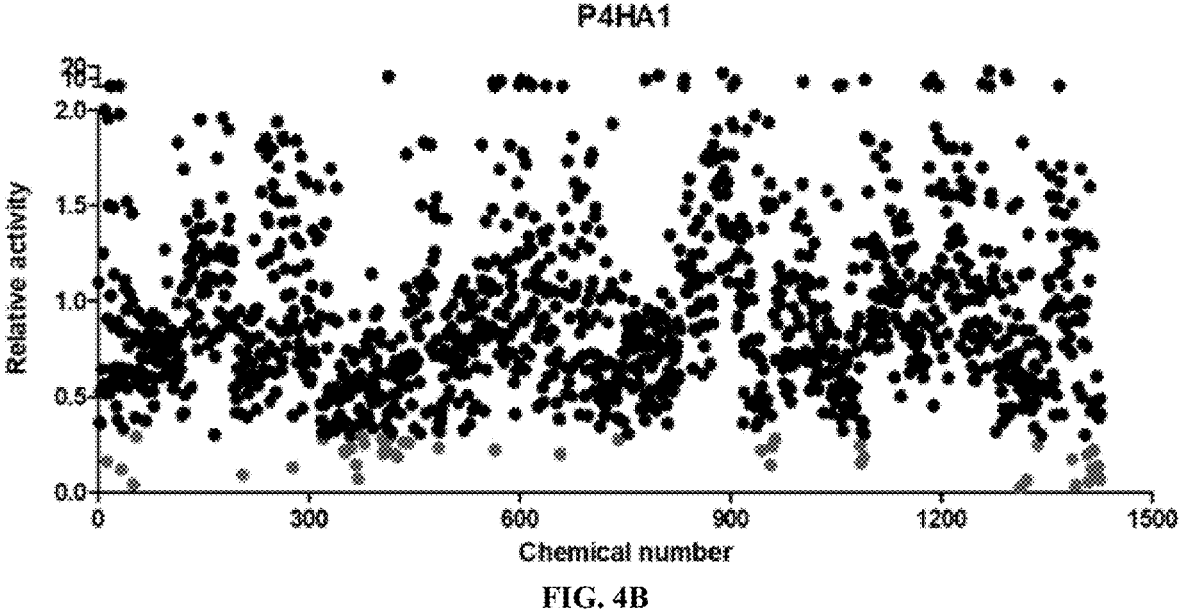
Figure 4C:
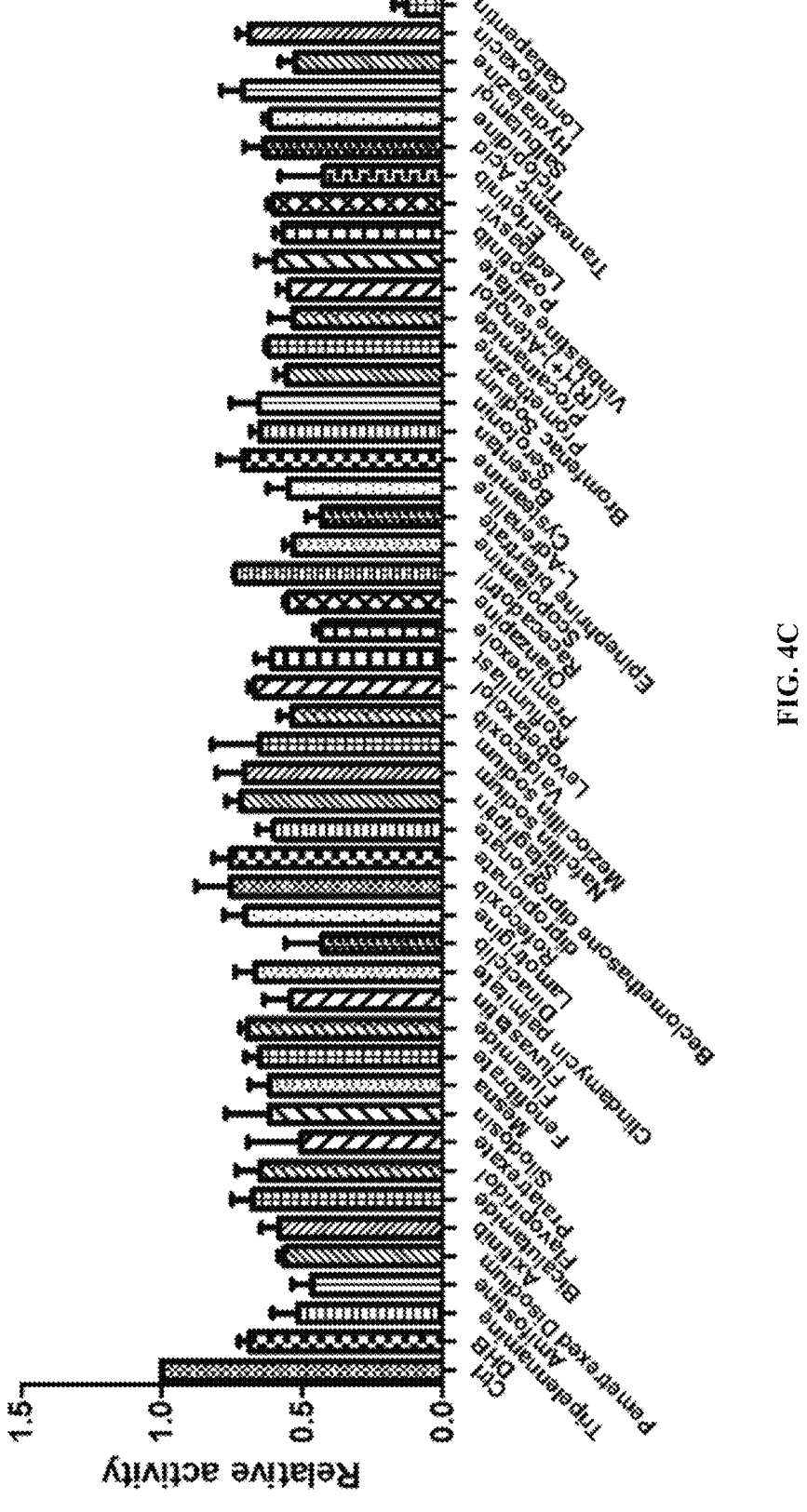
Figure 4D:
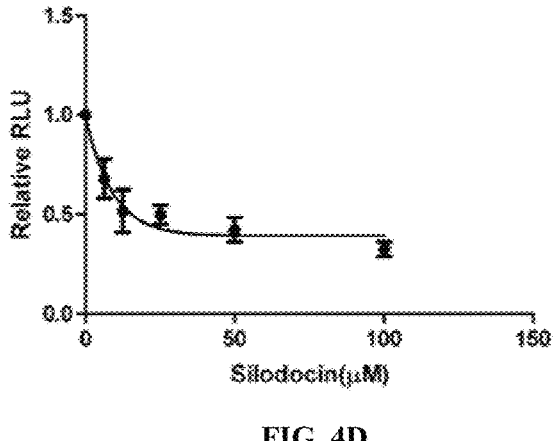
Figure 4E:
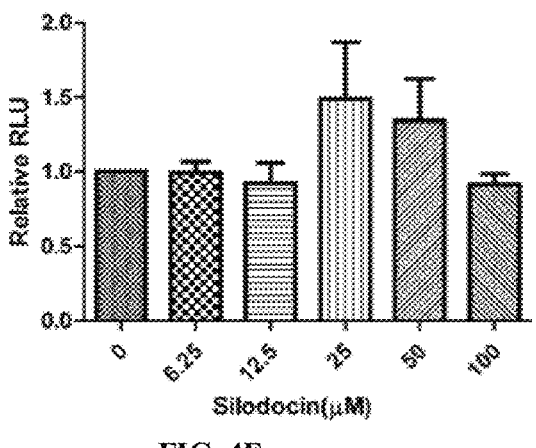
Figure 4F:
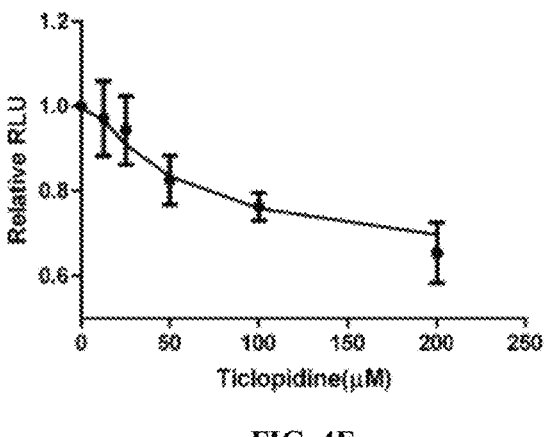
Figure 4G:
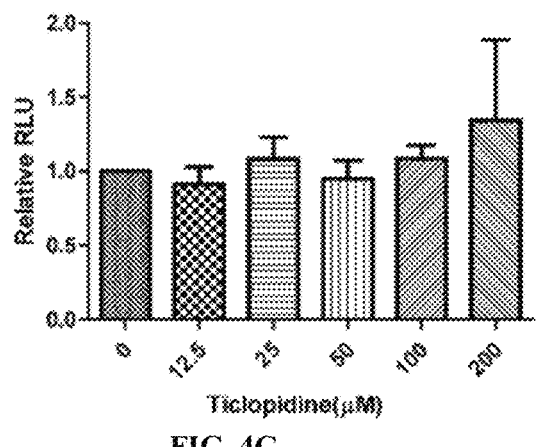
FIG. 4G. Ticlopidine did not inhibit the Succinate-Glo™ Hydroxylase assay in the absence of WT-P4H1; n=3.
Figure 4H:
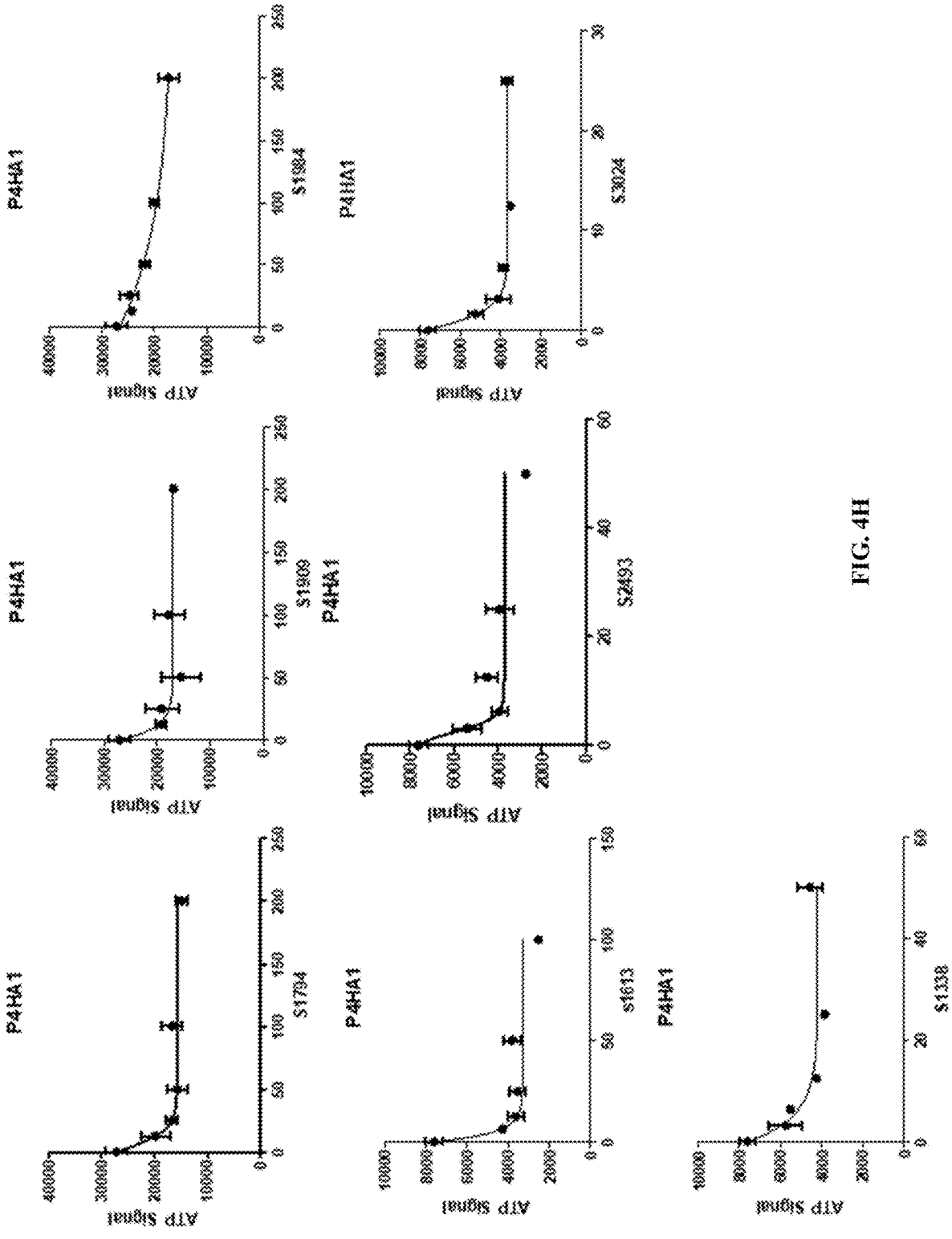
FIG. 4H. Dose curves for the enumerated chemicals.
Figure 4I:
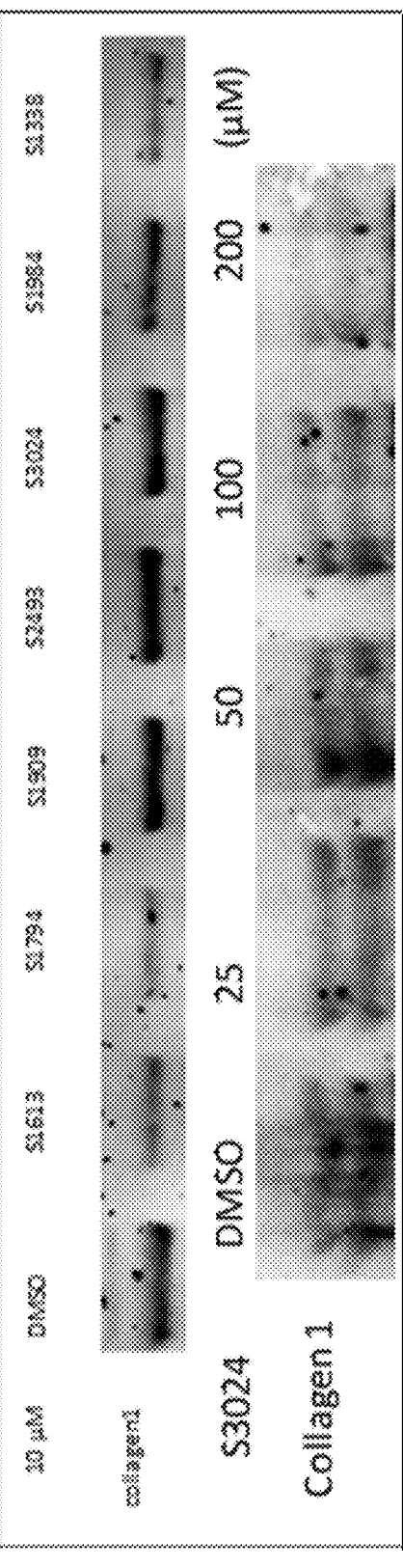
FIG. 4I. HS578 cells treated with compounds. The collagen I in the conditioned medium was detected by western blot. HS578 cells were treated with 10 μM chemicals and higher concentration of 53024 (Lamotrigine).

14 pidine were further tested, at different concentration. 47 chemicals (FIG. 4B) were found that exhibited inhibitory activity to C-P4H1 at 50 μM. The 47 inhibitory chemicals were further verified by triple assay (FIG. 4C) Both drugs inhibited C-P4H1 activity in a dose-dependent manner (FIG. 4D and FIG. 4F). Interestingly, Silodosin showed a faster kinetic property compared to ticlopidine, suggesting the different chemical-protein interaction mechanism between two drugs. The two chemicals had little effect on the luminescence assay in the absence of C-P4H1 (FIG. 4E and FIG. 4G), indicating that Silodosin and Ticlopidine specifically inhibited the C-P4H1 activity in vitro. Selected chemicals were shown the inhibitory activity at dose dependent manner. (FIG. 4I). The secreted collagen I in the conditioned medium was decrease when the HS578 cells were treated with 10 μM selected chemicals (FIG. 4I).

Figures 5A, 5B, 5C, 5D:
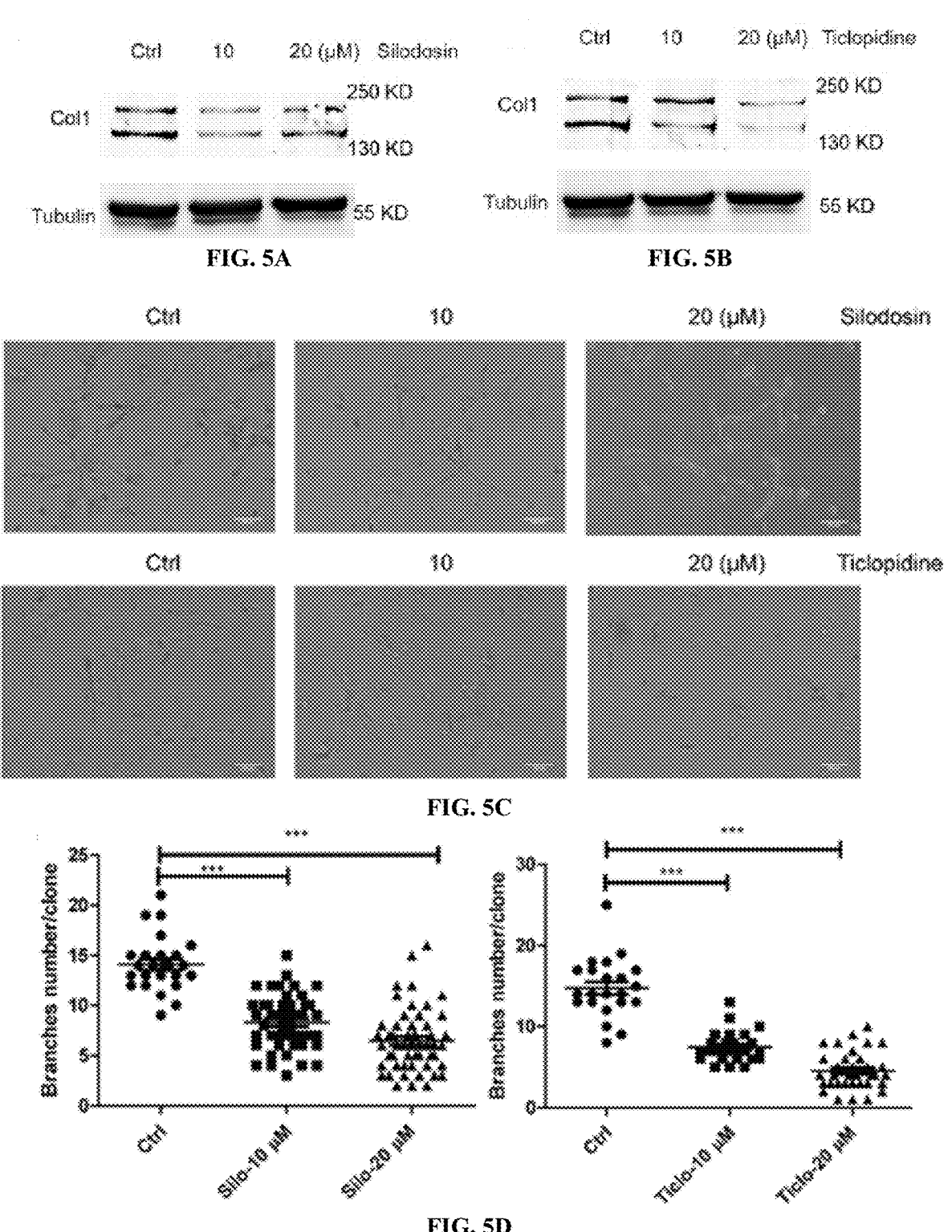
FIGS. 5A-5F show Silodocin and ticlopidine inhibit collagen deposition and cancer cell invasion.

To determine whether the identified potential inhibitors suppress the C-P4H1 activity in tissue culture, HS-578T cells were treated with Silodosin or Ticlopidine for 48 hours. Since collagen maturation and secretion was regulated by the C-P4H1, conditioned media were collected from control and Silodosin- or Ticlopidine-treated cells for western blot analysis. Treatment with Silodosin or Ticlopidine reduced protein levels of type I collagen in the conditioned media (FIGS. 5A and 5B). These results suggest that Silodosin and Ticlopidine can be uptake by cancer cells and inhibit C-P4H1 activity in vivo.

Figures 5E, 5F:
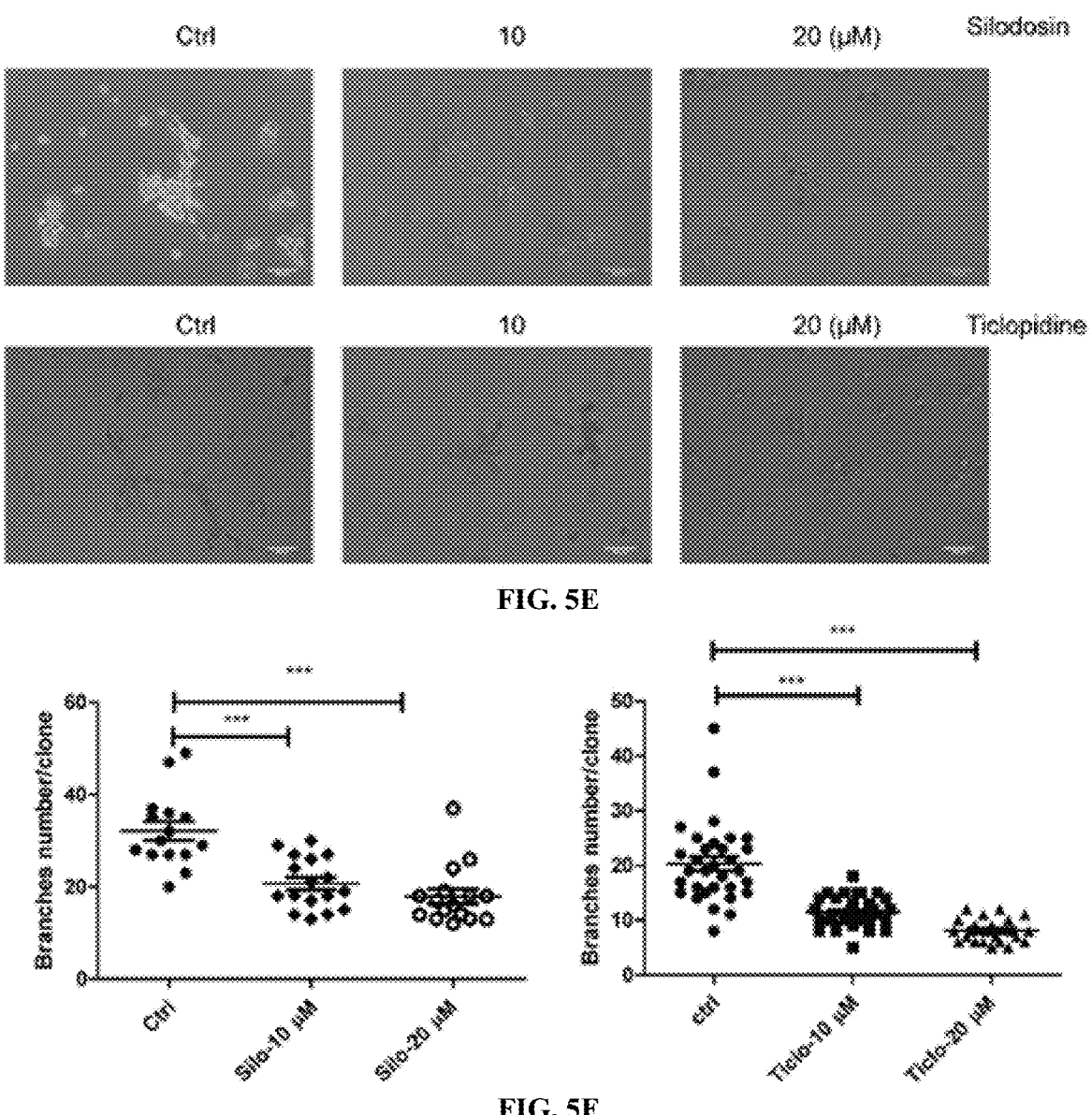

It has been shown that silence of P4HAs suppress invasive tumor growth in three-dimensional (3D) tissue culture model[19,25]. 3D culture model has been widely used to evaluate drug effect[38]. To further evaluate the inhibitory ability of these chemicals in tumor progression, triple-negative breast cancer cell lines, MDA-MB-231 cells and HS-578T cells were treated with Silodosin and Ticlopidine in 3D culture[39]. Both chemicals significantly reduced invasive branching structures of MDA-MB-231 cells (FIGS. 5C and 5D) and HS-578T cells (FIGS. 5E and 5F) in 3D culture. Invasive branching structure of cancer cells in 3D culture is associated with tumor invasion and aggressive phenotypes[15, 19, 25]. Knocking down P4HA1 inhibited invasive branching in triple-negative breast cancer cells but had very little effect on cell proliferation[19, 25]. To test whether Silodosin or Ticlopidine treatment inhibits tumor cell proliferation, the MDA-MB-231 and HS-578T cells were incubated with these two drugs and analyzed cell number and viability with CCK-8 kit. These results demonstrate that the C-P4H1 inhibitors identified from the Succinate-Glo™ assay suppressed invasive phenotypes of triple-negative breast cancer cells.

Figure 6:
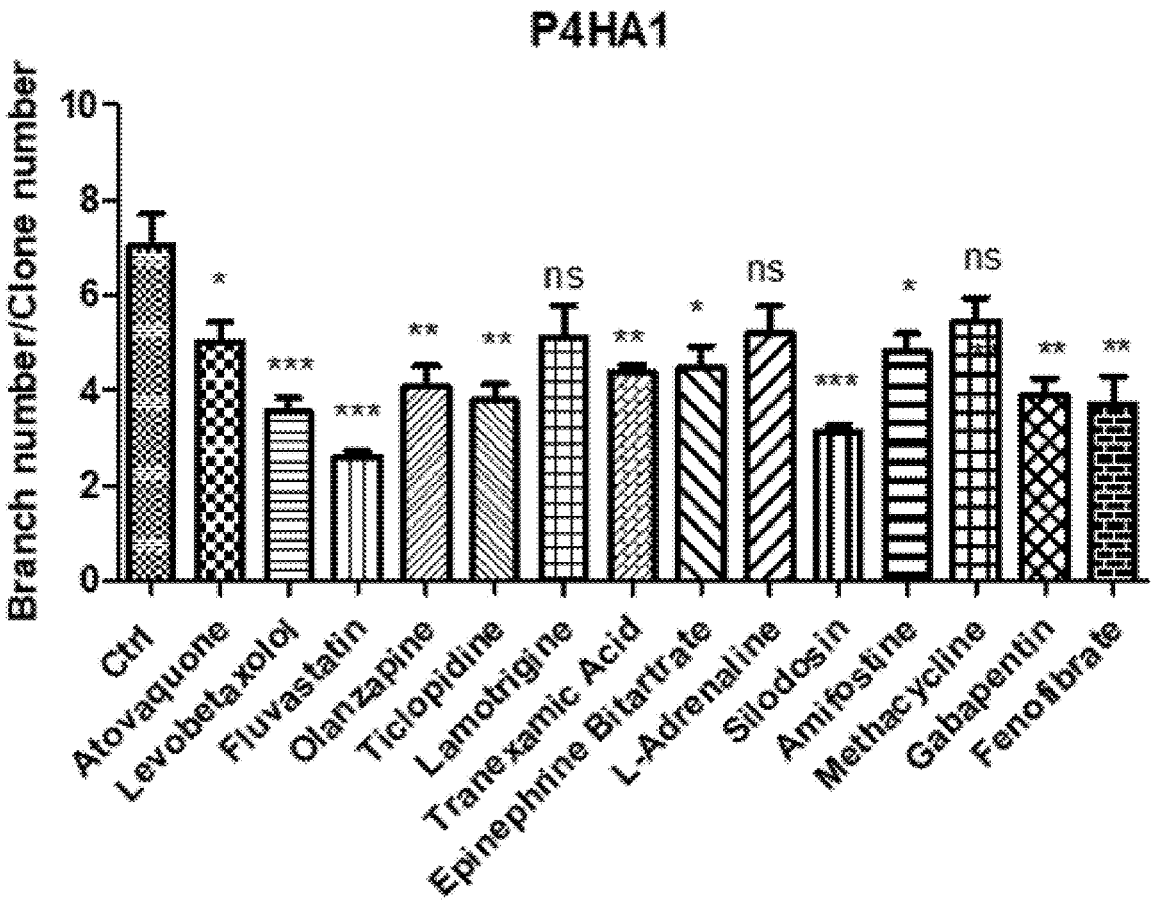
FIG. 6 shows inhibitory activity of compounds on breast cancer progression. In inhibitory activity of the C-P4HA1 inhibitors on breast cancer progression in 3D culture. MDA-MB-231 cells were treated with the chemicals in 3D culture for 3 days, and invasive growth was quantified under microscope.
Figure 7:
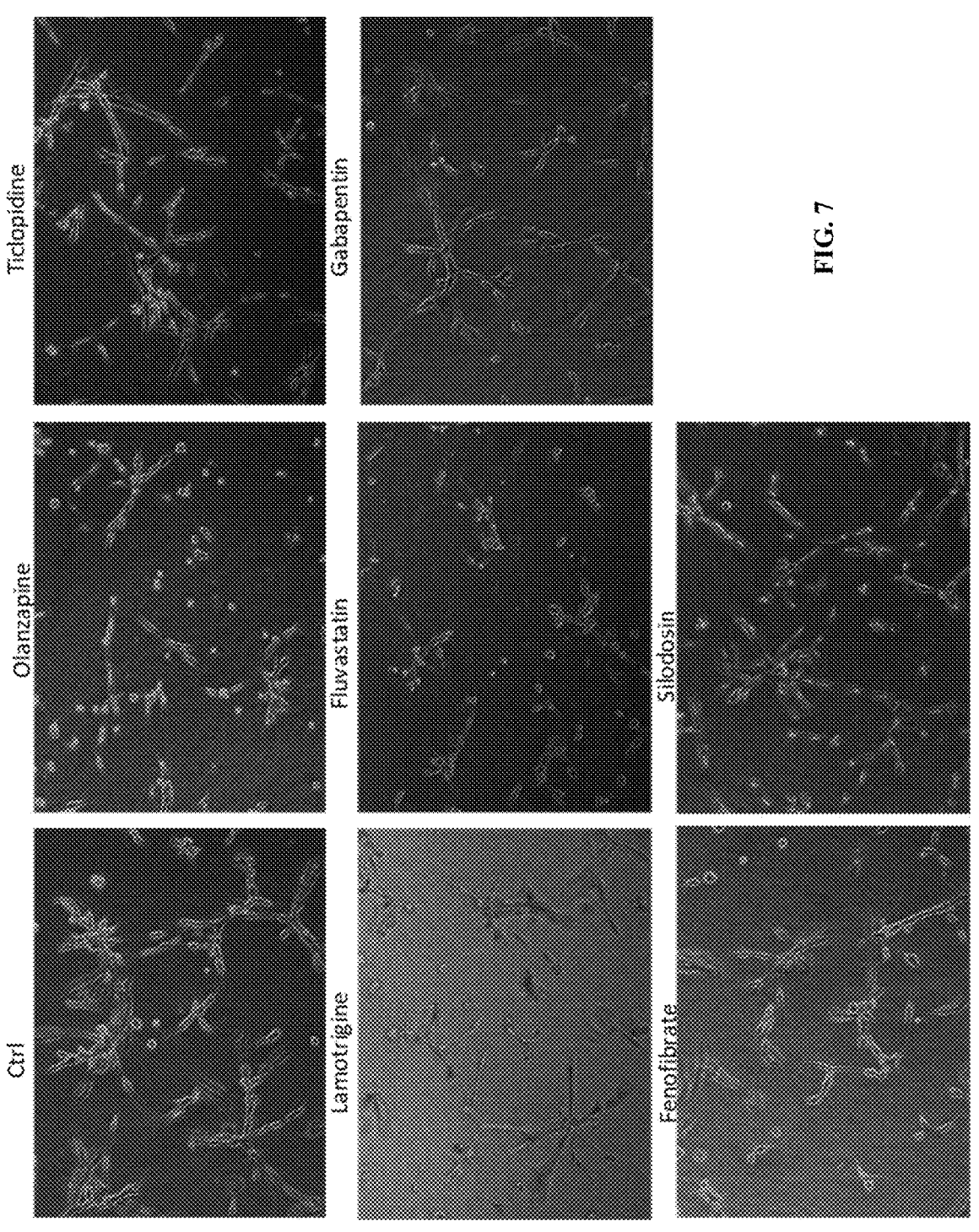
FIG. 7 shows microscopic images of breast cancer cells treated with indicated molecules.

To further evaluate the inhibitory ability of these chemicals, MDA-MB-231 cells were treated with the identified inhibitors in 3D culture. 14 chemicals significantly inhibited tumor progression in 3D culture (FIG. 6 and FIG. 7). These results demonstrate that identified chemicals can also inhibit C-P4H1 activity in tissue culture.

Figure 8:
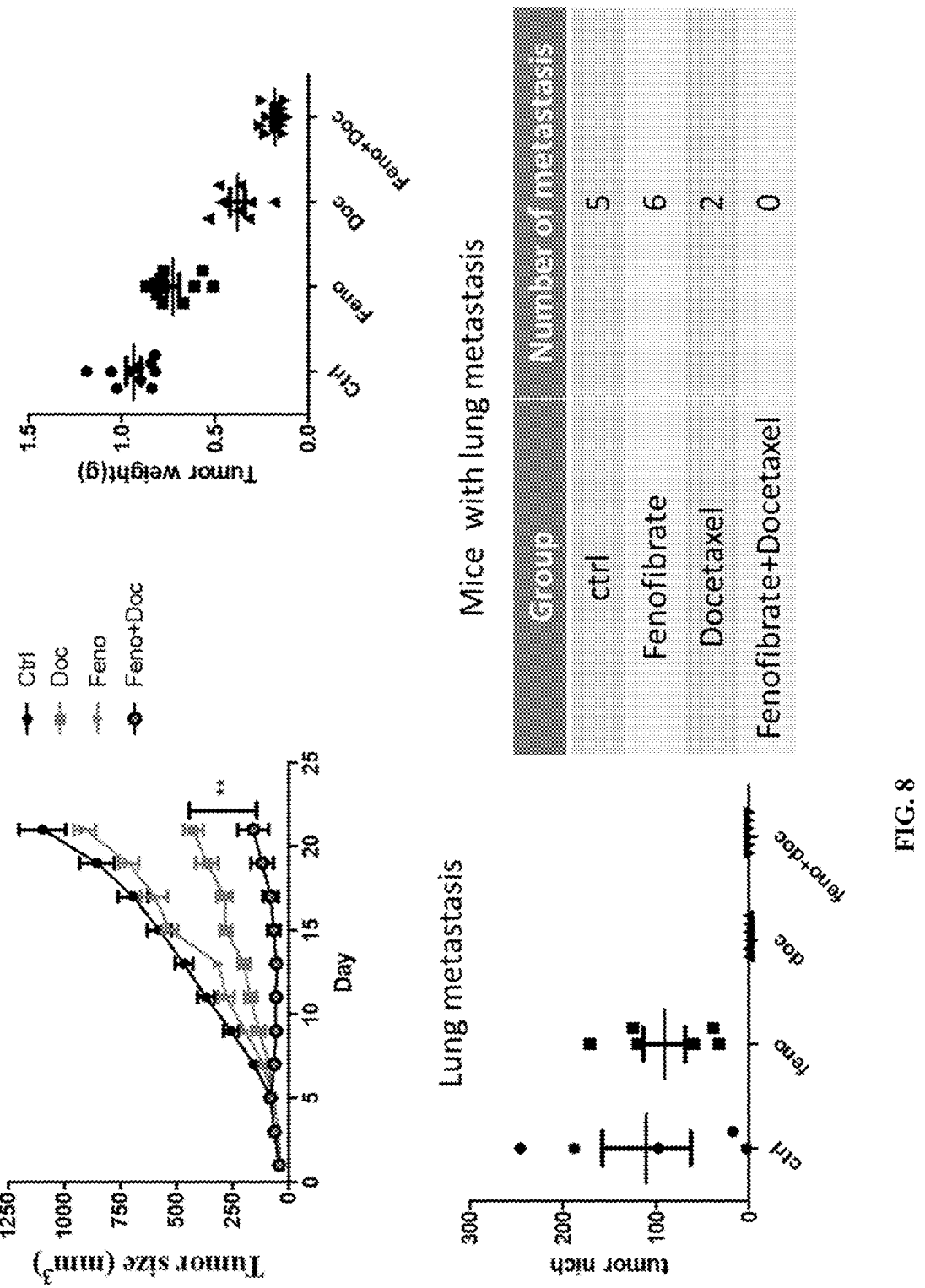
FIG. 8 shows fenofibrate was given every day orally since the tumor size was around 60 mm³. Meanwhile, docetaxel was given (i.p.) every four days. Remove the tumors when the control group tumor size reach 1000 mm³. 4 weeks later, take out the lungs, HE staining and quantify metastasis niches.
Figure 9:
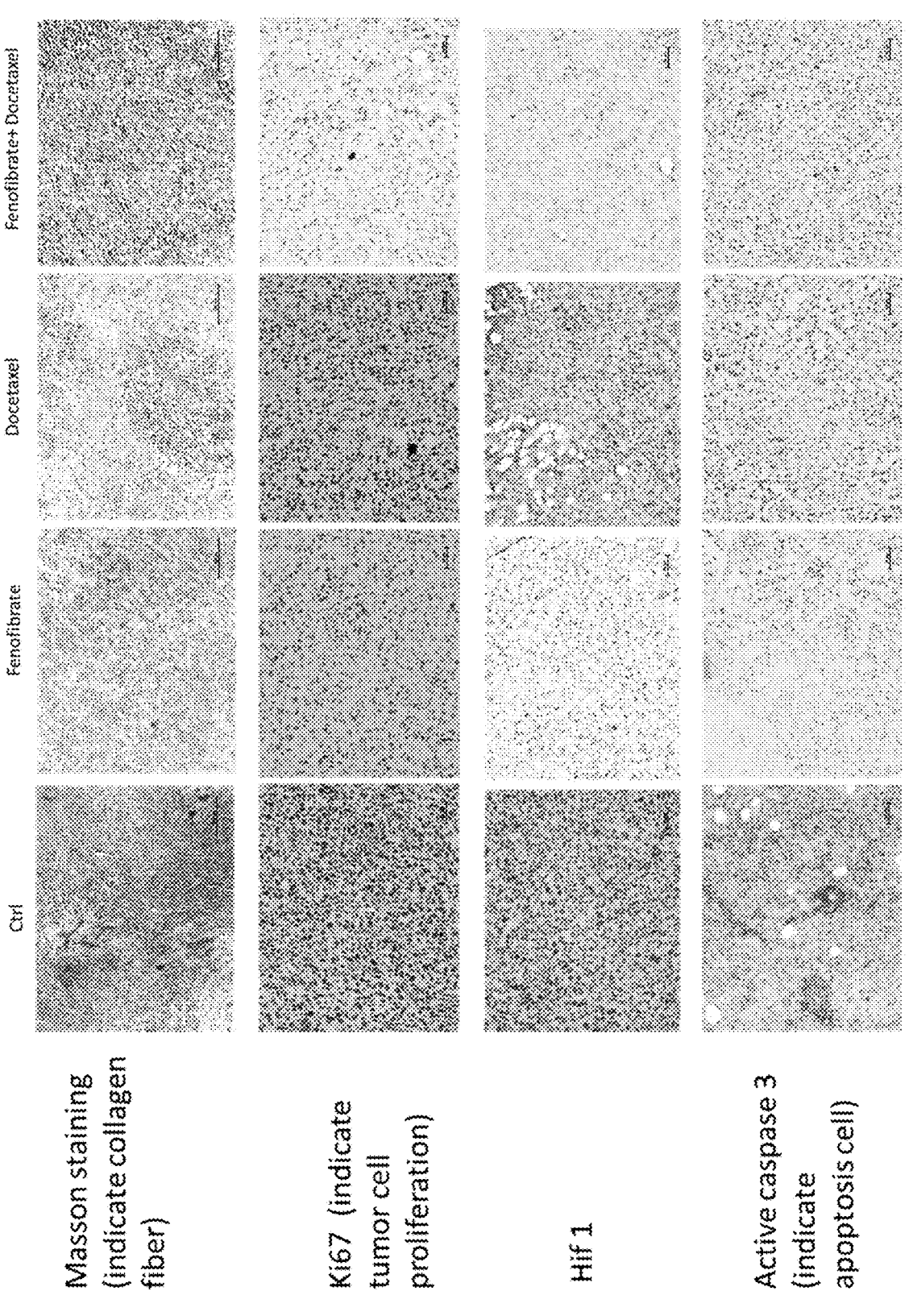
FIG. 9 shows (MDA-MB-231 xenograft) treated with vehicle control, (40 mg/kg) fenobibrate, (10 mg/kg) docetaxel, or fenofibrate and docetaxel.

Fenofibrate can also be administered in combination with Docetaxel to reduce the chemoresistance and lung metastasis in animals (FIG. 8). Fenofibrate reduces tumor size and weight compared to treatment with docetaxel alone. The effect of Fenofibrate is also apparent from images of various cancer cells (FIG. 9).

Figure 10:
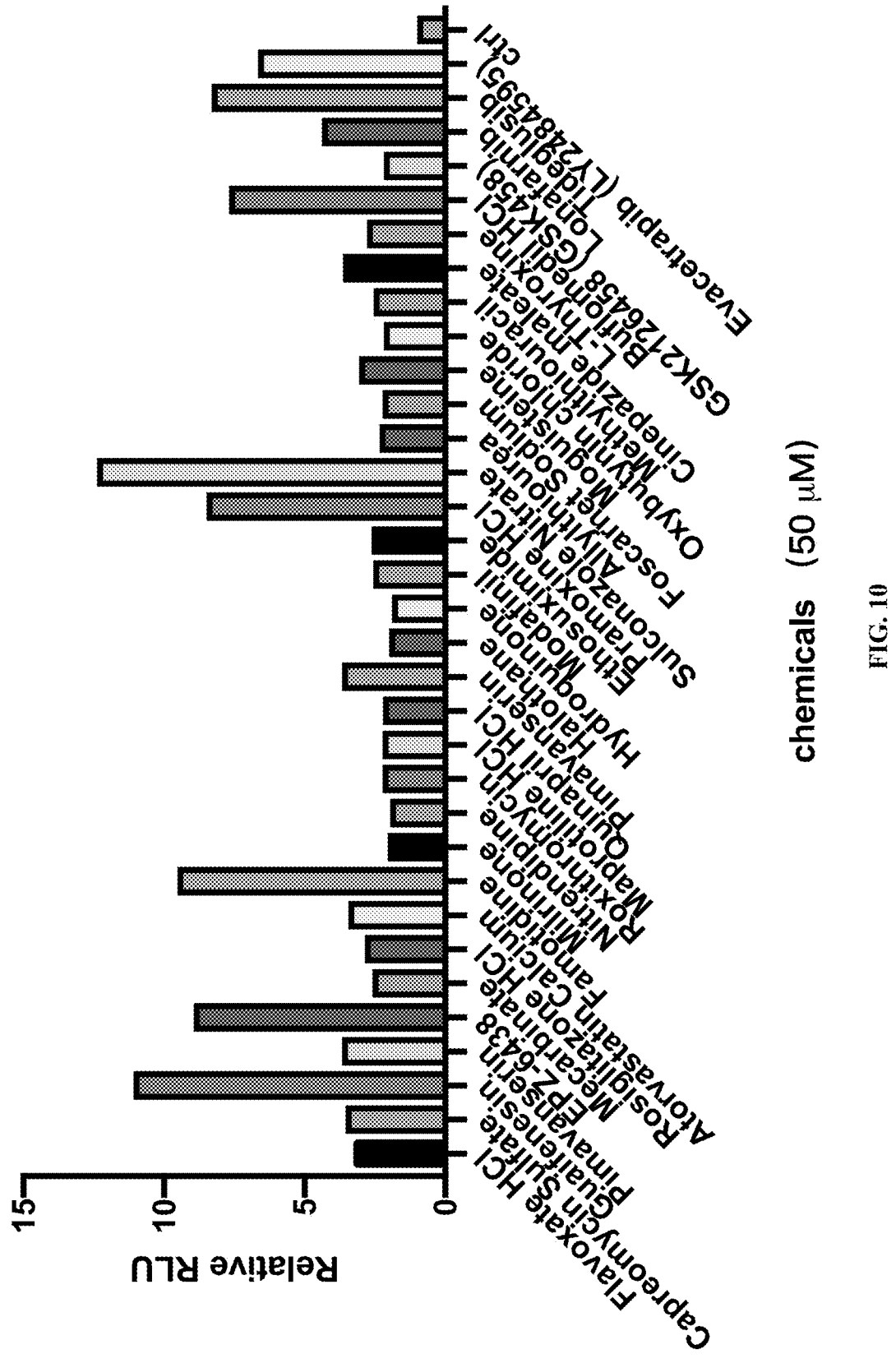
FIG. 10 shows C-P4H1 activators are identified with the high-throughput screening assay from the FDA-approved drug library (test compounds). in vitro activity of C-P4HA1 treated with 50 μM test compounds. 50 μM DHB was used as a positive control in each plate.

FIG. 10 shows C-P4H1 activators identified with the high-throughput screening assay from the FDA-approved drug library (test compounds). in vitro activity of C-P4HA1 treated with 50 μM compounds.

Methods were developed as disclosed herein to quantify C-P4H1 activity by measuring succinate levels. Using the high throughput screening assay based on these methods, several new C-P4H1 inhibitors were identified, including Silodosin and Ticlopidine, from the FDA-approved drug library. Treatment with Silodosin and Ticlopidine was confirmed to reduce collagen secretion and to suppress invasive phenotypes of breast cancer cells in 3D culture.

To develop a better method to quantify the C-P4H1 activity, the hydroxyproline colorimetric assay to measure hydroxyproline and Succinate-Glo™ Hydroxylase assay to measure succinate levels were compared. The latter was found to be more sensitive for measuring the C-P4H1 activity. One potential reason for the reduced sensitivity in the hydroxylation colorimetric assay is the short peptide length and Pro position of the substrate compared to collagen protein[40]. Thus, using longer peptide as a substrate may increase the hydroxylation reaction rate and improve the colorimetric assay sensitivity. As mentioned above, HPLC has been used to identify small molecules that inhibit the C-P4H1 activity. Compared with the HPLC-based assay, the method that was developed with Succinate-Glo™ Hydroxylase assay is contemplated for large scale screening.

Using the Succinate-Glo™ Hydroxylase assay, more than 40 potential C-P4H1 inhibitors were identified from the FDA-approved drug library. These inhibitors have been used for the treatment of various diseases, but the majority of them have not been tested in collagen-related diseases. Interestingly, a number of chemicals enhanced the enzyme activity, indicating that this method can be used to identify potential C-P4H1 activators. Collagen deficiency is associated with tissue adhesion diseases, including Ehlers-Danlos Syndrome and Osteoporosis[41]. Enhancing collagen producing by inducing C-P4H1 activity is a potential strategy for the treatment of these diseases.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Myllyharju, J.; Kivirikko, K. I., Collagens, modifying enzymes and their mutations in humans, flies and worms. Trends Genet 2004, 20 (1), 33-43.
2. Levental, K. R.; Yu, H.; Kass, L.; Lakins, J. N.; Egeblad, M.; Erler, J. T.; Fong, S. F.; Csiszar, K.; Giaccia, A.; Weninger, W.; Yamauchi, M.; Gasser, D. L.; Weaver, V. M., Matrix crosslinking forces tumor progression by enhancing integrin signaling. Cell 2009, 139 (5), 891-906.
3. Provenzano, P. P.; Inman, D. R.; Eliceiri, K. W.; Knittel, J. G.; Yan, L.; Rueden, C. T.; White, J. G.; Keely, P. J., Collagen density promotes mammary tumor initiation and progression. BMC Med 2008, 6, 11.
4. Specks, U.; Nerlich, A.; Colby, T. V.; Wiest, I.; Timpl, R., Increased expression of type VI collagen in lung fibrosis. Am J Respir Crit Care Med 1995, 151 (6), 1956-64.
5. Ricard-Blum, S., The collagen family. Cold Spring Harb Perspect Biol 2011, 3 (1), a004978.
6. Jenkins, C. L.; Bretscher, L. E.; Guzei, I. A.; Raines, R. T., Effect of 3-hydroxyproline residues on collagen stability. J Am Chem Soc 2003, 125 (21), 6422-7.
7. Gorres, K. L.; Raines, R. T., Prolyl 4-hydroxylase. Crit Rev Biochem Mol Biol 2010, 45 (2), 106-24.
8. Anantharajan, J.; Koski, M. K.; Kursula, P.; Hieta, R.; Bergmann, U.; Myllyharju, J.; Wierenga, R. K., The structural motifs for substrate binding and dimerization of the alpha subunit of collagen prolyl 4-hydroxylase. Structure 2013, 21 (12), 2107-18.

9. Annunen, P.; Autio-Harmainen, H.; Kivirikko, K. I., The novel type II prolyl 4-hydroxylase is the main enzyme form in chondrocytes and capillary endothelial cells, whereas the type I enzyme predominates in most cells. J Biol Chem 1998, 273 (11), 5989-92.

10. Zhou, Z. H.; Ji, C. D.; Xiao, H. L.; Zhao, H. B.; Cui, Y. H.; Bian, X. W., Reorganized Collagen in the Tumor Microenvironment of Gastric Cancer and Its Association with Prognosis. J Cancer 2017, 8 (8), 1466-1476.

11. Cloos, P. A.; Christgau, S.; Lyubimova, N.; Body, J. J.; Qvist, P.; Christiansen, C., Breast cancer patients with bone metastases are characterised by increased levels of nonisomerised type I collagen fragments. Breast Cancer Res 2003, 5 (4), R103-9.

12. Ewald, J. A.; Downs, T. M.; Cetnar, J. P.; Ricke, W. A., Expression microarray meta-analysis identifies genes associated with Ras/MAPK and related pathways in progression of muscle-invasive bladder transition cell carcinoma. PLoS One 2013, 8 (2), e55414.

13. Liu, W.; Li, L.; Ye, H.; Tao, H.; He, H., Role of COL6A3 in colorectal cancer. Oncol Rep 2018, 39 (6), 2527-2536.

14. Carafoli, F.; Hohenester, E., Collagen recognition and transmembrane signalling by discoidin domain receptors. Biochim Biophys Acta 2013, 1834 (10), 2187-94.

15. Zhang, H.; Fredericks, T.; Xiong, G.; Qi, Y.; Rychahou, P. G.; Li, J. D.; Pihlajaniemi, T.; Xu, W.; Xu, R., Membrane associated collagen XIII promotes cancer metastasis and enhances anoikis resistance. Breast Cancer Res 2018, 20 (1), 116.

16. Hanker, A. B.; Estrada, M. V.; Bianchini, G.; Moore, P. D.; Zhao, J.; Cheng, F.; Koch, J. P.; Gianni, L.; Tyson, D. R.; Sanchez, V.; Rexer, B. N.; Sanders, M. E.; Zhao, Z.; Stricker, T. P.; Arteaga, C. L., Extracellular Matrix/Integrin Signaling Promotes Resistance to Combined Inhibition of HER2 and PI3K in HER2(+) Breast Cancer. Cancer Res 2017, 77 (12), 3280-3292.

17. Lai, S. L.; Tan, M. L.; Hollows, R. J.; Robinson, M.; Ibrahim, M.; Margielewska, S.; Parkinson, E. K.; Ramanathan, A.; Zain, R. B.; Mehanna, H.; Spruce, R. J.; Wei, W.; Chung, I.; Murray, P. G.; Yap, L. F.; Paterson, I. C., Collagen Induces a More Proliferative, Migratory and Chemoresistant Phenotype in Head and Neck Cancer via DDR1. Cancers (Basel) 2019, 11 (11).

18. Lee, Y. C.; Kurtova, A. V.; Xiao, J.; Nikolos, F.; Hayashi, K.; Tramel, Z.; Jain, A.; Chen, F.; Chokshi, M.; Lee, C.; Bao, G.; Zhang, X.; Shen, J.; Mo, Q.; Jung, S. Y.; Rowley, D.; Chan, K. S., Collagen-rich airway smooth muscle cells are a metastatic niche for tumor colonization in the lung. Nat Commun 2019, 10 (1), 2131.

19. Xiong, G.; Stewart, R. L.; Chen, J.; Gao, T.; Scott, T. L.; Samayoa, L. M.; O'Connor, K.; Lane, A. N.; Xu, R., Collagen prolyl 4-hydroxylase 1 is essential for HIF-1alpha stabilization and TNBC chemoresistance. Nat Commun 2018, 9 (1), 4456.

20. Bickel, M.; Baringhaus, K. H.; Gerl, M.; Gunzler, V.; Kanta, J.; Schmidts, L.; Stapf, M.; Tschank, G.; Weidmann, K.; Werner, U., Selective inhibition of hepatic collagen accumulation in experimental liver fibrosis in rats by a new prolyl 4-hydroxylase inhibitor. Hepatology 1998, 28 (2), 404-11.

21. Cao, X. Q.; Liu, X. X.; Li, M. M.; Zhang, Y.; Chen, L.; Wang, L.; Di, M. X.; Zhang, M., Overexpression of Prolyl-4-Hydroxylase-alpha1 Stabilizes but Increases Shear Stress-Induced Atherosclerotic Plaque in Apolipoprotein E-Deficient Mice. Dis Markers 2016, 2016, 1701637.

22. Gorres, K. L.; Raines, R. T., Direct and continuous assay for prolyl 4-hydroxylase. Anal Biochem 2009, 386 (2), 181-5.

23. Vasta, J. D.; Andersen, K. A.; Deck, K. M.; Nizzi, C. P.; Eisenstein, R. S.; Raines, R. T., Selective Inhibition of Collagen Prolyl 4-Hydroxylase in Human Cells. ACS Chem Biol 2016, 11 (1), 193-9.

24. Vasta, J. D.; Raines, R. T., Selective inhibition of prolyl 4-hydroxylases by bipyridinedicarboxylates. Bioorg Med Chem 2015, 23 (13), 3081-90.

25. Xiong, G.; Deng, L.; Zhu, J.; Rychahou, P. G.; Xu, R., Prolyl-4-hydroxylase alpha subunit 2 promotes breast cancer progression and metastasis by regulating collagen deposition. BMC Cancer 2014, 14, 1.

26. Koivu, J.; Myllyla, R., Protein disulfide-isomerase retains procollagen prolyl 4-hydroxylase structure in its native conformation. Biochemistry 1986, 25 (20), 5982-6.

27. Vuori, K.; Pihlajaniemi, T.; Marttila, M.; Kivirikko, K. I., Characterization of the human prolyl 4-hydroxylase tetramer and its multifunctional protein disulfide-isomerase subunit synthesized in a baculovirus expression system. Proc Natl Acad Sci USA 1992, 89 (16), 7467-70.

28. Neubauer, A.; Neubauer, P.; Myllyharju, J., High-level production of human collagen prolyl 4-hydroxylase in *Escherichia coli*. Matrix Biol 2005, 24 (1), 59-68.

29. Baldi, L.; Hacker, D. L.; Adam, M.; Wurm, F. M., Recombinant protein production by large-scale transient gene expression in mammalian cells: state of the art and future perspectives. Biotechnol Lett 2007, 29 (5), 677-84.

30. Neuman, R. E.; Logan, M. A., The determination of hydroxyproline. J Biol Chem 1950, 184 (1), 299-306.

31. Stegemann, H.; Stalder, K., Determination of hydroxyproline. Clin Chim Acta 1967, 18 (2), 267-73.

32. Edwards, C. A.; O'Brien, W. D., Jr., Modified assay for determination of hydroxyproline in a tissue hydrolyzate. Clin Chim Acta 1980, 104 (2), 161-7.

33. Guo, H. F.; Cho, E. J.; Devkota, A. K.; Chen, Y.; Russell, W.; Phillips, G. N., Jr.; Yamauchi, M.; Dalby, K. N.; Kurie, J. M., A scalable lysyl hydroxylase 2 expression system and luciferase-based enzymatic activity assay. Arch Biochem Biophys 2017, 618, 45-51.

34. Lamberg, A.; Pihlajaniemi, T.; Kivirikko, K. I., Site-directed mutagenesis of the alpha subunit of human prolyl 4-hydroxylase. Identification of three histidine residues critical for catalytic activity. J Biol Chem 1995, 270 (17), 9926-31.

35. Majamaa, K.; Gunzler, V.; Hanauske-Abel, H. M.; Myllyla, R.; Kivirikko, K. I., Partial identity of the 2-oxoglutarate and ascorbate binding sites of prolyl 4-hydroxylase. J Biol Chem 1986, 261 (17), 7819-23.

36. Franklin, T. J.; Hitchen, M., Inhibition of collagen hydroxylation by 2,7,8-trihydroxyanthraquinone in embryonic-chick tendon cells. Biochem J 1989, 261 (1), 127-30.

37. Hernandez, J. J.; Pryszlak, M.; Smith, L.; Yanchus, C.; Kurji, N.; Shahani, V. M.; Molinski, S. V., Giving Drugs a Second Chance: Overcoming Regulatory and Financial Hurdles in Repurposing Approved Drugs As Cancer Therapeutics. Front Oncol 2017, 7, 273.

38. Li, L.; Chen, J.; Xiong, G.; St Clair, D. K.; Xu, W.; Xu, R., Increased ROS production in non-polarized mammary epithelial cells induces monocyte infiltration in 3D culture. J Cell Sci 2017, 130 (1), 190-202.

39. Kenny, P. A.; Lee, G. Y.; Myers, C. A.; Neve, R. M.; Semeiks, J. R.; Spellman, P. T.; Lorenz, K.; Lee, E. H.; Barcellos-Hoff, M. H.; Petersen, 0. W.; Gray, J. W.; Bissell, M. J., The morphologies of breast cancer cell lines in three-dimensional assays correlate with their profiles of gene expression. Mol Oncol 2007, 1 (1), 84-96.

40. Kivirikko, K. I.; Kishida, Y.; Sakakibara, S.; Prockop, D. J., Hydroxylation of (X-Pro-Gly)n by protocollagen proline hydroxylase. Effect of chain length, helical conformation and amino acid sequence in the substrate. Biochim Biophys Acta 1972, 271 (2), 347-56.

41. Manon-Jensen, T.; Kjeld, N. G.; Karsdal, M. A., Collagen-mediated hemostasis. J Thromb Haemost 2016, 14 (3), 438-48.

42. Kellogg, G. E.; Semus, S. F., 3D QSAR in modern drug design. EXS 2003, (93), 223-41.

43. Verma, J.; Khedkar, V. M.; Coutinho, E. C., 3D-QSAR in drug design—a review. Curr Top Med Chem 2010, 10 (1), 95-115.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of screening for modulators of C-P4H1, comprising:

(a) expressing a P4H1 complex in a eukaryotic cell;

(b) purifying the P4H1 complex;

(c) adding the purified P4H1 complex to a well of a high throughput assay plate;

(d) adding peptide substrate GlyProProGlyOEt, $FeSO_4$, catalase, ascorbate, and $\alpha$-ketoglutarate to the well of the high throughput assay plate;

(e) adding a test molecule or control to the well of the high throughput assay plate;

(f) adding 3-oxoacid CoA-transferase (SCOT) and succinyl CoA ligase (SCS), in the presence of acetoacetyl-CoA to convert succinate into ATP to the well of the high throughput assay plate;

(g) adding luciferase to convert ATP into light energy to the well of the high throughput assay plate;

(h) measuring luminescence of the well of the high throughput assay plate; and (i) identifying a molecule as a modulator of P4H1 when the molecule increases luminescence of the well relative to negative control or decreases luminescence of the well relative to positive control.

* * * * *